(12) United States Patent
Bartkovitz et al.

(10) Patent No.: US 7,994,321 B2
(45) Date of Patent: Aug. 9, 2011

(54) SUBSTITUTED THIENO[3,2-C]PYRIDINE-7-CARBOXYLIC ACID DERIVATIVES

(75) Inventors: David Joseph Bartkovitz, Nutley, NJ (US); Yi Chen, Nutley, NJ (US); Xin-Jie Chu, Livingston, NJ (US); Kin-Chun Luk, North Caldwell, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 1038 days.

(21) Appl. No.: 11/780,603

(22) Filed: Jul. 20, 2007

(65) Prior Publication Data

US 2008/0045562 A1 Feb. 21, 2008

Related U.S. Application Data

(60) Provisional application No. 60/836,360, filed on Aug. 8, 2006.

(51) Int. Cl.
*C07D 513/04* (2006.01)
*A61K 31/4365* (2006.01)
(52) U.S. Cl. ........................ 546/114; 514/301
(58) Field of Classification Search .................. 546/114; 514/301

See application file for complete search history.

(56) References Cited

U.S. PATENT DOCUMENTS

2005/0256154 A1 11/2005 Luk et al.

FOREIGN PATENT DOCUMENTS

| WO | WO 2004/100947 A2 | 11/2004 |
| WO | WO 2005/010009 A1 | 2/2005 |
| WO | WO 2005/105809 | 11/2005 |
| WO | WO 2006/106326 A1 | 10/2006 |

OTHER PUBLICATIONS

Michelotti et. al. "Two classes of p38a MAP kinase inhibitors having a common diphenylether core but exhibiting divergent binding modes" Bioorganic & Medicinal Chemistry Letters 2005, 15, 5274-5279.*

Jiang et. al. "3,5-Disubstituted quinolines as novel c-Jun N-terminal kinase inhibitors." Bioorganic & Medicinal Chemistry Letters 2007, 17, 6378-6382.*
Liu et. al. "Synthesis and SAR of 1,9-dihydro-9-hydroxypyrazolo[3,4-b]quinolin-4-ones as novel, selective c-Jun N-terminal kinase inhibitors" Bioorganic & Medicinal Chemistry Letters 2006, 16, 2590-2594.*
Miyazaki et. al. "Design and effective synthesis of novel templates, 3,7-diphenyl-4- amino-thieno and furo-[3,2-c]pyridines as protein kinase inhibitors and in vitro evaluation targeting angiogenetic kinases" Bioorganic & Medicinal Chemistry Letters 2007, 17, 250-254.*
Mulvihill et. al. "Novel 2-phenylquinolin-7-yl-derived imidazo[1,5-a]pyrazines as potent insulin-like growth factor-I receptor (IGF-IR) inhibitors" Bioorganic & Medicinal Chemistry 2008, 16, 1359-1375.*
Mulvihill et. al. "1,3-Disubstituted-imidazo[1,5-a]pyrazines as insulin-like growth-factor-I receptor (IGF-IR) inhibitors" Bioorganic & Medicinal Chemistry Letters 2007, 17, 1091-1097.*
Blackburn et. al. "Discovery and optimization of N-acyl and N-aroylpyrazolines as B-Raf kinase inhibitors" Bioorganic & Medicinal Chemistry Letters 20 (2010) 4795-4799.*
Strumberg and Seeber, Onkologie, 2005, 28: 101-107.
Beeram et al, J. Clin. Oncol. 2005, 23: 6771-6790.
Bollag et al, Current Opinion in Investigational Drugs, 2003, 4: 1436-1441.
Sharma et al, Cancer Res. 2005, 2412-2421.
Roberts et al, Cancer Research, 2005, 65(3), 957-966.
Ho et al., J. Med. Chem., 2005, 48, 8163-8173.

* cited by examiner

*Primary Examiner* — Janet Andres
*Assistant Examiner* — David K O Dell
(74) *Attorney, Agent, or Firm* — George W. Johnston; Patricia S. Rocha-Tramaloni

(57) ABSTRACT

There are provided compounds of the formula

I

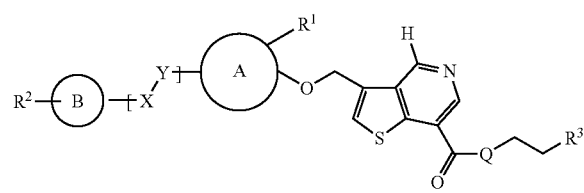

wherein $R^1$, $R^2$, $R^3$, X, Y, Q, Ring A and Ring B are as described.
The compounds exhibit activity as anticancer agents.

10 Claims, No Drawings

SUBSTITUTED THIENO[3,2-C]PYRIDINE-7-CARBOXYLIC ACID DERIVATIVES

PRIORITY TO RELATED APPLICATION(S)

This application claims the benefit of U.S. Provisional Application No. 60/836,360, filed Aug. 8, 2006, which is hereby incorporated by reference in its entirety.

BACKGROUND OF THE INVENTION

Many disease states are characterized by uncontrolled proliferation and differentiation of cells. These disease states encompass a variety of cell types and maladies such as cancer, atherosclerosis, and restenosis. In many such disease states kinases, important cellular enzymes that perform essential functions by regulating cell division and proliferation, appear to play a decisive role.

The molecular mechanisms and signaling pathways that regulate cell proliferation and survival are receiving considerable attention as potential targets for anticancer strategies. Recently, there has been a notable increase in efforts directed at targeting the MAPK pathway, which integrates a wide array of proliferative signals initiated by receptor tyrosine kinases (RTKs) and G protein-coupled receptors.

The MAPK signal cascade includes the G protein Ras working upstream of a core module consisting of 3 kinases: Raf phosphorylates and thus activates MEK1/2, which in turn ultimately leads to the activation of ERK1/2. Raf kinase has long been considered an attractive target for drug discovery due to its importance as a potential checkpoint for cancer-related signal transduction (Strumberg and Seeber, Onkologie, 2005, 28: 101-107; Beeram et al., J. Clin. Oncol. 2005, 23: 6771-6790). The importance of the MAPK signaling cascade for the proliferation and survival of tumor cells recently increased with the discovery of activating B-Raf mutations in human tumors. Activating Raf mutations have been identified in melanoma, thyroid, colon, and other cancers (Strumberg and Seeber, Onkologie, 2005, 28: 101-107; Bollag et al., Current Opinion in Investigational Drugs, 2003, 4:1436-1441).

Therefore, in addition to a role in controlling tumors with Ras mutations and activated growth factor receptors, inhibitors of Raf kinase may harbor therapeutic potential in tumors carrying a B-Raf oncogene (Sharma et al., Cancer Res. 2005, 65: 2412-2421).

The mammalian Raf serine/threonine kinase family consists of three 68- to 74-kd proteins termed A-Raf, B-Raf, and C-Raf (Raf-1), which share highly conserved amino-terminal regulatory regions and catalytic domains at the carboxyl terminus. Raf proteins are normally cytosolic but they are recruited to the plasma membrane by the small G-protein Ras, and this is an essential step for their activation by growth factors, cytokines, and hormones. At the membrane, Raf activation occurs through a highly complex process involving conformation changes, binding to other proteins, binding to lipids, and phosphorylation and dephosphorylation of some residues.

A variety of agents have been discovered to interfere with Raf kinase, including antisense oligonucleotides and small molecules. These inhibitors prevent the expression of Raf protein, block Ras/Raf interaction, or obstruct its kinase activity. Down regulation of B-Raf activity by siRNA or through the kinase inhibitor BAY-43-9006 leads to inhibition of the growth of melanoma cells and siRNA-mediated reduction of B-Raf led to decreased tumorigenic potential of 1205 Lu cells. Raf inhibitors that are currently undergoing clinical evaluation show promising signs of anti-cancer efficacy with a very tolerable safety profile. Clinically most advanced is the Raf inhibitor BAY 43-9006, which has recently been approved by the FDA for treatment of metastatic renal cell carcinoma with additional phase III clinical testing for treatment of other cancers.

Further it has been found that receptor tyrosine kinases represent large enzymes that span the cell membrane and possess an extracellular binding domain for growth factors such as epidermal growth factor, a transmembrane domain, and an intracellular portion that functions as a kinase to phosphorylate specific tyrosine residue in proteins and hence to influence cell proliferation. The foregoing tyrosine kinases may be classified as growth factor receptor (e.g. EGFR, PDGFR, FGFR and erbB2) or non-receptor (e.g. c-src and bcr-abl) kinases. It is known that such kinases are often aberrantly expressed in common human cancers such as breast cancer, gastrointestinal cancer such as colon, rectal or stomach cancer, leukemia, and ovarian, bronchial or pancreatic cancer (Roberts et al., Cancer Research, 2005, 65(3), 957-966 and Ho et al., J. Med. Chem., 2005, 48, 8163-8173).

Despite the progress that has been made, the search continues for low molecular weight compounds that target Raf or PDGFR associated kinases and are therefore useful for treating a wide variety of tumors and other proliferative disorders including restenosis, angiogenesis, diabetic retinopathy, psoriasis, surgical adhesions, macular degeneration, and atherosclerosis. Thus, a strong need exists to provide compositions, pharmaceuticals and/or medicaments with anti-proliferative activity. Such compositions, pharmaceuticals and/or medicaments may possess not only strong activity, but also exert diminished side effects in comparison to other anti-proliferative agents. Furthermore, the spectrum of tumors responsive to treatment with such compositions, pharmaceuticals and/or medicaments may be broad. Active ingredients of this type may be suitable in the mentioned indication as single agent, and/or in combination therapy, be it in connection with other therapeutic agents, with radiation, with operative/surgical procedures, heat treatment or any other treatment known in the mentioned indications.

SUMMARY OF THE INVENTION

The present invention relates to compounds of the formula

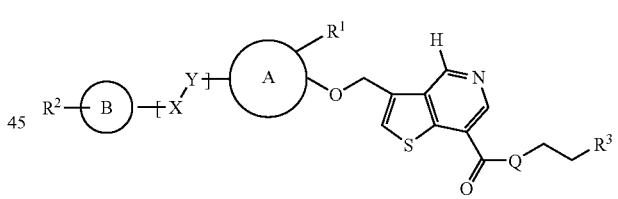

I wherein $R^1$, $R^2$, $R^3$, X, Y, Q, A and B are as herein described. These compounds are believed to inhibit tyrosine kinases related to PDGFR or Raf and as such the compounds will have anti-angiogenic or anti-hyperproliferative cellular, e.g. anti-cancer, activity.

DETAILED DESCRIPTION OF THE INVENTION

The present compounds are new compounds of the formula

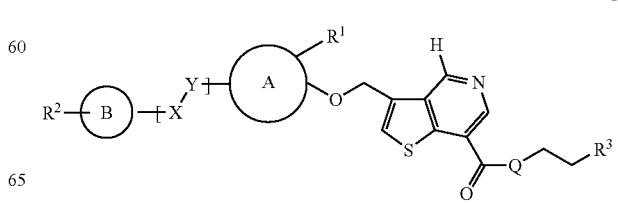

I wherein
R¹ is selected from the group consisting of hydrogen, lower alkyl, lower alkenyl, lower alkynyl, lower alkoxy, cyano, NR⁴R⁵, trifluoromethyl and NO₂;
R² is selected from the group consisting of hydrogen, lower alkyl, substituted lower alkyl, aryl or heteroaryl substituted lower alkyl, lower alkenyl, lower alkynyl, lower alkoxy, aryl, substituted aryl, heteroaryl, substituted heteroaryl, cyano, halogen, methyl sulfonyl, sulfonamide, trifluoromethyl, sulfonyl urea, amide, ester, carbamoyl, carbamate, NR⁴R⁵ and urea;
R³ is selected from the group consisting of hydrogen, lower alkyl, hydroxyl, substituted lower alkyl, lower alkoxy and NR⁴R⁵;
R⁴ and R⁵ are selected from hydrogen, lower alkyl or lower alkyl substituted by hydroxyl or lower alkoxy;
Q is O or NH;
Ring A and Ring B are aryl, heteroaryl or substituted heteroaryl;
Linker X—Y is selected from the group consisting of —OCH₂—, —CH₂O—, —NHCO—, —CONH—, —O—, —OCH₂CH₂—, —CH₂OCH₂—, —CH₂CH₂O—, —CF=CH—, —CH=CF—, —NH—, —NHCH₂—, —CH₂NH—, —SCH₂—, —CH₂S—, —SOCH₂—, —CH₂SO—, —SO₂CH₂—, —NHSO₂—, —SO₂NH— —CH₂SO₂—, —S—, —CH=CH— and lower alkyl or X—Y can be a simple bond;
with the proviso that when X—Y is a simple bond, Ring B is a substituted heteroaryl selected from the group consisting of

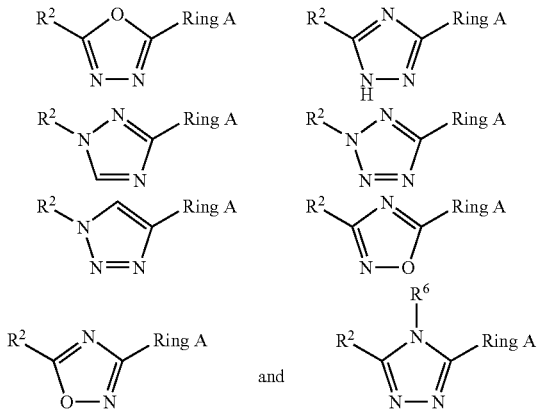

wherein R⁶ is a lower alkyl substituted by hydroxyl.
with said rings being optionally further substituted and the pharmaceutically acceptable salts thereof.

Preferred compounds are those wherein X—Y are selected from the group consisting of —OCH₂—, —CH₂O—, —NHCO— and —CONH—.

Also preferred are compounds wherein X—Y is a simple bond.

Also preferred are compounds where ring A is phenyl or pyridinyl.

More preferred are compounds where Ring A is 2,5-disubstituted phenyl.

Also more preferred are compounds where Ring A is 3-hydroxy-2,5-disubstituted pyridinyl.

Also preferred are compounds wherein R¹ is selected from the group consisting of —CH₃, —Cl and —F.

Further preferred are compounds wherein R² is selected from the group consisting of —Cl, —F, —CF₃, —CONH₂, lower alkoxy, NR⁴R⁵, and lower alkyl.

Ring B can be substituted by 1-3 R² which are independently selected from the R² group defined above.

Especially preferred are compounds of the formula
3-[3-(4-Chloro-benzoylamino)-phenoxymethyl]-thieno[3,2-c]pyridine-7-carboxylic acid ethyl ester,
3-[3-(4-Chloro-benzoylamino)-phenoxymethyl]-thieno[3,2-c]pyridine-7-carboxylic acid (2-hydroxy-ethyl)-amide,
3-(3-Benzoylamino-phenoxymethyl)-thieno[3,2-c]pyridine-7-carboxylic acid ethyl ester,
3-(3-Benzoylamino-phenoxymethyl)-thieno[3,2-c]pyridine-7-carboxylic acid (2-hydroxy-ethyl)-amide,
3-[3-(4-Fluoro-benzoylamino)-phenoxymethyl]-thieno[3,2-c]pyridine-7-carboxylic acid ethyl ester,
3-[3-(4-Fluoro-benzoylamino)-phenoxymethyl]-thieno[3,2-c]pyridine-7-carboxylic acid (2-hydroxy-ethyl)-amide,
3-{3-[4-(2-Hydroxy-ethylamino)-benzoylamino]-phenoxymethyl}-thieno[3,2-c]pyridine-7-carboxylic acid (2-hydroxy-ethyl)-amide,
3-[3-(3-Chloro-benzoylamino)-phenoxymethyl]-thieno[3,2-c]pyridine-7-carboxylic acid ethyl ester,
3-[3-(2-Chloro-benzoylamino)-phenoxymethyl]-thieno[3,2-c]pyridine-7-carboxylic acid ethyl ester,
3-[3-(2-Fluoro-benzoylamino)-phenoxymethyl]-thieno[3,2-c]pyridine-7-carboxylic acid ethyl ester,
3-[3-(3-Methoxy-benzoylamino)-phenoxymethyl]-thieno[3,2-c]pyridine-7-carboxylic acid ethyl ester,
3-[3-(2-Methoxy-benzoylamino)-phenoxymethyl]-thieno[3,2-c]pyridine-7-carboxylic acid ethyl ester,
3-[3-(4-Methoxy-benzoylamino)-phenoxymethyl]-thieno[3,2-c]pyridine-7-carboxylic acid ethyl ester,
3-[3-(3-Chloro-benzoylamino)-phenoxymethyl]-thieno[3,2-c]pyridine-7-carboxylic acid (2-hydroxy-ethyl)-amide,
3-[3-(2-Chloro-benzoylamino)-phenoxymethyl]-thieno[3,2-c]pyridine-7-carboxylic acid (2-hydroxy-ethyl)-amide,
3-[3-(2-Fluoro-benzoylamino)-phenoxymethyl]-thieno[3,2-c]pyridine-7-carboxylic acid (2-hydroxy-ethyl)-amide,
3-[3-(3-Methoxy-benzoylamino)-phenoxymethyl]-thieno[3,2-c]pyridine-7-carboxylic acid (2-hydroxy-ethyl)-amide,
3-[3-(4-Methoxy-benzoylamino)-phenoxymethyl]-thieno[3,2-c]pyridine-7-carboxylic acid (2-hydroxy-ethyl)-amide,
3-[3-(2-Hydroxy-benzoylamino)-phenoxymethyl]-thieno[3,2-c]pyridine-7-carboxylic acid (2-hydroxy-ethyl)-amide,
3-[5-(3-Chloro-benzoylamino)-2-methyl-phenoxymethyl]-thieno[3,2-c]pyridine-7-carboxylic acid ethyl ester,
3-[5-(3-Chloro-benzoylamino)-2-methyl-phenoxymethyl]-thieno[3,2-c]pyridine-7-carboxylic acid (2-hydroxy-ethyl)-amide,
3-[5-(3-Chloro-benzoylamino)-2-methyl-phenoxymethyl]-thieno[3,2-c]pyridine-7-carboxylic acid (2-hydroxy-ethyl)-amide, toluene-4-sulfonic acid salt,
3-[5-(3-Fluoro-benzoylamino)-2-methyl-phenoxymethyl]-thieno[3,2-c]pyridine-7-carboxylic acid ethyl ester,
3-[5-(4-Fluoro-benzoylamino)-2-methyl-phenoxymethyl]-thieno[3,2-c]pyridine-7-carboxylic acid ethyl ester,
3-[5-(3-Methoxy-benzoylamino)-2-methyl-phenoxymethyl]-thieno[3,2-c]pyridine-7-carboxylic acid ethyl ester,
3-[5-(4-Fluoro-benzoylamino)-2-methyl-phenoxymethyl]-thieno[3,2-c]pyridine-7-carboxylic acid (2-hydroxy-ethyl)-amide,
3-[5-(3-Methoxy-benzoylamino)-2-methyl-phenoxymethyl]-thieno[3,2-c]pyridine-7-carboxylic acid (2-hydroxy-ethyl)-amide,
4-Chloro-3-[2-methyl-5-(5-methyl-[1,3,4]oxadiazol-2-yl)-phenoxymethyl]-thieno[3,2-c]pyridine-7-carboxylic acid ethyl ester, 3-[2-Methyl-5-(5-methyl-[1,3,4]oxadiazol-2-yl)-phenoxymethyl]-thieno[3,2-c]pyridine-7-carboxylic acid ethyl ester and 3-{5-[4-(2-Hydroxy-ethyl)-5-methyl-4H-[1,2,4]triazol-3-yl]-2-methyl-phenoxymethyl}-thieno[3,2-c]pyridine-7-carboxylic acid (2-hydroxy-ethyl)-amide.

In the specification, where indicated, the various groups may be substituted by 1-5 or, preferably, 1-3 substituents independently selected from the group consisting of lower alkyl, lower-alkenyl, lower-alkynyl, dioxo-lower-alkylene (forming e.g. a benzodioxyl group), halogen, hydroxy, CN, $CF_3$, $NH_2$, N(H, lower-alkyl), N(lower-alkyl)$_2$, aminocarbonyl, carboxy, $NO_2$, lower-alkoxy, thio-lower-alkoxy, lower-alkylsulfonyl, aminosulfonyl, lower-alkylcarbonyl, lower-alkylcarbonyloxy, lower-alkoxycarbonyl, lower-alkyl-carbonyl-NH, fluoro-lower-alkyl, fluoro-lower-alkoxy, lower-alkoxy-carbonyl-lower-alkoxy, carboxy-lower-alkoxy, carbamoyl-lower-alkoxy, hydroxy-lower-alkoxy, $NH_2$-lower-alkoxy, N(H, lower-alkyl)-lower-alkoxy, N(lower-alkyl)$_2$-lower-alkoxy, benzyloxy-lower-alkoxy, mono- or di-lower alkyl substituted amino-sulfonyl and lower-alkyl which can optionally be substituted with halogen, hydroxy, $NH_2$, N(H, lower-alkyl) or N(lower-alkyl)$_2$. Preferred substituents for the alkyl, aryl, heteroaryl and heterocycle rings are halogen, lower alkoxy, lower alkyl and amino.

The term "alkyl" refers to straight- or branched-chain saturated hydrocarbon groups having from 1 to about 20 carbon atoms, including groups having from 1 to about 7 carbon atoms. In certain embodiments, alkyl substituents may be lower alkyl substituents. The term "lower alkyl" refers to alkyl groups having from 1 to 6 carbon atoms, and in certain embodiments from 1 to 4 carbon atoms. Examples of alkyl groups include, but are not limited to, methyl, ethyl, n-propyl, i-propyl, n-butyl, s-butyl, t-butyl, n-pentyl, and s-pentyl.

As used herein, "cycloalkyl" is intended to refer to any stable monocyclic or polycyclic system which consists of carbon atoms only, any ring of which being saturated, and the term "cycloalkenyl" is intended to refer to any stable monocyclic or polycyclic system which consists of carbon atoms only, with at least one ring thereof being partially unsaturated. Examples of cycloalkyls include, but are not limited to, cyclopropyl, cyclobutyl, cyclopentyl, cyclohexyl, cycloheptyl, adamantyl, cyclooctyl, bicycloalkyls, including bicyclooctanes such as [2.2.2]bicyclooctane or [3.3.0]bicyclooctane, bicyclononanes such as [4.3.0]bicyclononane, and bicyclodecanes such as [4.4.0]bicyclodecane (decalin), or spiro compounds. Examples of cycloalkenyls include, but are not limited to, cyclopentenyl or cyclohexenyl.

The term "alkenyl" as used herein means an unsaturated straight-chain or branched aliphatic hydrocarbon group containing one double bond and having 2 to 6, preferably 2 to 4 carbon atoms. Examples of such "alkenyl group" are vinyl (ethenyl), allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl.

The term "alkynyl" as used herein means an unsaturated straight-chain or branched aliphatic hydrocarbon group containing one triple bond and having 2 to 6, preferably 2 to 4 carbon atoms. Examples of such "alkynyl group" are ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

The term "halogen" as used in the definitions means fluorine, chlorine, bromine, or iodine, preferably fluorine and chlorine.

"Aryl" means a monovalent, monocyclic or bicyclic, aromatic carbocyclic hydrocarbon radical, preferably a 6-10 member aromatic ring system. Preferred aryl groups include, but are not limited to, phenyl, naphthyl, tolyl, and xylyl.

"Heteroaryl" means an aromatic ring system having at least one heteroatom and containing up to two rings. Preferred heteroaryl groups include, but are not limited to, thienyl, furyl, indolyl, pyrrolyl, pyridinyl, pyrazinyl, oxazolyl, thiaxolyl, quinolinyl, pyrimidinyl, imidazole and tetrazolyl.

In the case of aryl or heteroaryl which are bicyclic it should be understood that one ring may be aryl while the other is heteroaryl and both being substituted or unsubstituted.

"Amide" refers to the following group: —(C=O)—$NR^aR^b$, wherein $R^a$ and $R^b$ are independently hydrogen or lower alkyl. An example of an amide group is carbamoyl: —(C=O)—$NH_2$.

"Ester" refers to the following group: —(C=O)—O—$C_{1-6}$-alkyl.

"Sulfonamide" refers to the following group: —S(O)$_2$—$NR^aR^b$, wherein $R^a$ and $R^b$ are independently hydrogen or lower alkyl.

"Hetero atom" means an atom selected from N, O and S.

"Alkoxy, alkoxyl or lower alkoxy" refers to any of the above lower alkyl groups attached to an oxygen atom. Typical lower alkoxy groups include methoxy, ethoxy, isopropoxy or propoxy, butyloxy and the like. Further included within the meaning of alkoxy are multiple alkoxy side chains, e.g. ethoxy, methoxy ethoxy, methoxy ethoxy ethoxy and the like and substituted alkoxy side chains, e.g., dimethylamino ethoxy, diethylamino ethoxy, dimethoxy-phosphoryl methoxy and the like.

"Pharmaceutically acceptable," such as pharmaceutically acceptable carrier, excipient, etc., means pharmacologically acceptable and substantially non-toxic to the subject to which the particular compound is administered.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoro acetic acid and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., Ansel et al., Pharmaceutical Dosage Forms and Drug Delivery Systems (6th Ed. 1995) at pp. 196 and 1456-1457.

The compounds of formula I as well as their salts that have at least one asymmetric carbon atom may be present as racemic mixtures or different stereoisomers. The various isomers can be isolated by known separation methods, e.g., chromatography.

Compounds disclosed herein and covered by formula I above may exhibit tautomerism or structural isomerism. It is intended that the invention encompasses any tautomeric or structural isomeric form of these compounds, or mixtures of such forms, and is not limited to any one tautomeric or structural isomeric form depicted in formula I above.

The compounds of the present invention are useful in the treatment or control of cell proliferative disorders, in particular oncological disorders. These compounds and formulations containing said compounds may be useful in the treatment or control of solid tumors, such as, for example, breast, colon, lung and prostate tumors.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, as well as the particular mode of administration. The amount of active ingredient which can be combined with a carrier material to produce a single dosage form will generally be that amount of a formula I compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, sachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

"Effective amount" means an amount that is effective to prevent, alleviate or ameliorate symptoms of disease or prolong the survival of the subject being treated.

"$IC_{50}$" refers to the concentration of a particular compound required to inhibit 50% of a specific measured activity. $IC_{50}$ can be measured, inter alia, as is described subsequently.

"Pharmaceutically acceptable ester" refers to a conventionally esterified compound of formula I having a carboxyl group or hydroxy group, which esters retain the biological effectiveness and properties of the compounds of formula I and are cleaved in vivo (in the organism) to the corresponding active carboxylic acid or alcohol respectively.

Compounds of this invention can be synthesized according to the following general schemes.

Starting materials are available via commercial sources. Preparation of the azole building blocks are well known in the art. See e.g. Li, Z. et al. *J. Med. Chem.* 2005, 48, 6169. Some examples are listed below.

Scheme 1:

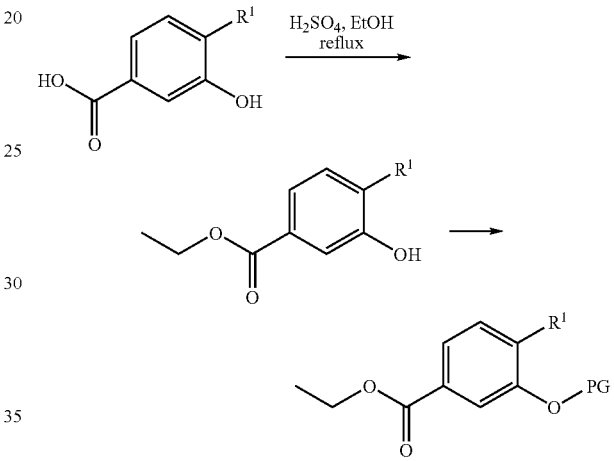

Esterification of intermediate acid can be performed by well known procedures such as heating the appropriate acid in ethanol or other corresponding alcohol in the presence of a mineral acid, such as sulfuric acid or hydrochloric acid, as catalyst.

In this application, R' is the required substituent needed to prepare compounds within this invention. Some examples are presented in the Examples section.

PG, PG' etc. are suitable protecting groups when necessary, but are not required. The use of such protecting groups is well known in the art of organic synthesis and can be introduced by well known experimental procedures. Such protecting groups can be, but are not limited to, t-butyldimethylsilyl, triphenylsilyl, 2-trimethylsilanyl-ethoxymethoxy, methoxymethoxy, 4-methoxy-benzyl. Methods for removing the various protecting groups are also well know in the art. See, e.g., Greene, T. W. and Wuts, P. G. M., *Protective Groups in Organic Synthesis* (3th Ed. 1999).

Scheme 2:

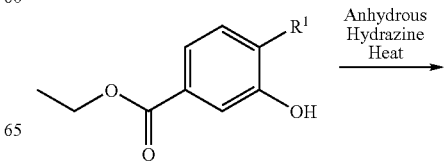

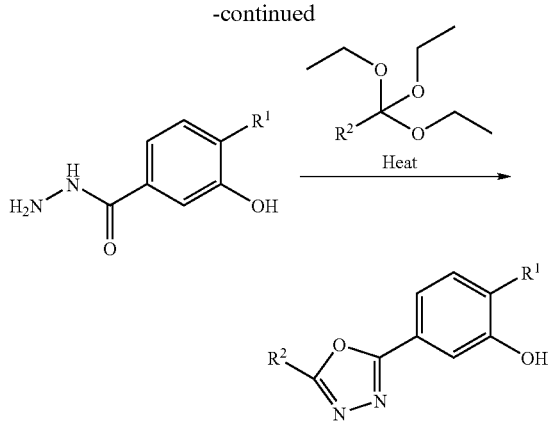

Conversion of the appropriate ester to the corresponding hydrazide can be achieved by heating a mixture of the ester in anhydrous hydrazine, for example at reflux. The hydrazide can be converted to the corresponding oxadiazole by heating, for example at reflux, a mixture of the hydrazide in the appropriate orthoesters, for example triethyl orthoacetate to give $R^2$ being methyl. See e.g. Schlecker, R. et al. *Tetrahedron* 1988, 44, 3289.

Scheme 3:

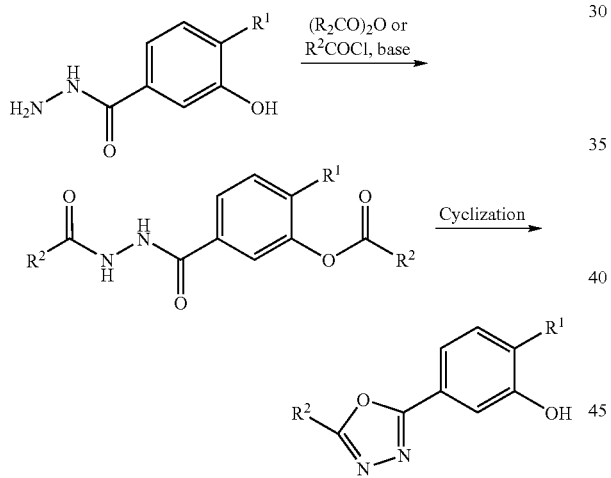

Alternately, appropriate oxadiazoles can be prepared from the corresponding hydrazide by first acylating the hydrazide with an acid anhydride or acid chloride in the presence of a base such as triethylamine, pyridine, diisopropylethyl-amine, or inorganic base such as sodium carbonate either neat or in a solvent such as dichloromethane, or acetonitrile. Such acylation can be achieved at reaction temperatures ranging from −30° C. to heating at reflux of the solvent, usually between 0° C. to room temperature. When present, the phenol can also be acylated and can be selective hydrolyzed by treatment with mild base such as dilute aqueous sodium hydroxide solution. The acyl hydrazide can be cyclized to form the corresponding oxadiazole by methods well known in the art and are not limited to the ones exemplified here. One such process could be treating the acylhydrazide with triphenylphosphine and hexachloroethane or carbon tetrabromide (see e.g. James, C. A. et al. *Tetrahedron Letters* 2006, 47, 511; Rajapakse, H. A. et al. *Tetrahedron Letters*, 2006, 47, 4827). In other method, heating the acylhydrazide with phosphorous oxychloride can also be employed (Balsells, J. et al. *Organic Letters* 2005, 7, 1039).

Scheme 4:

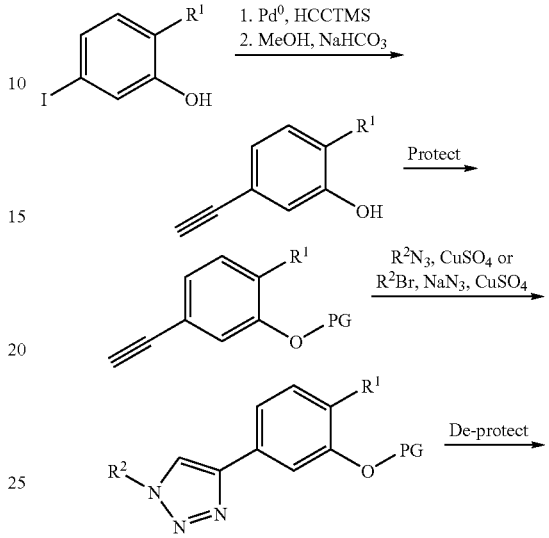

Methods for preparing aryl acetylene is well known I the art. One such method is palladium catalyzed coupling of trimethylsilylacetylene with aryl iodide. Such aryl acetylenes can be converted to the appropriate triazoles via copper salt catalyzed reaction with the aproate azide or sodium azide and the corresponding alkyl halide (see e.g. Appukkuttan, P. et al. *Organic Letters*, 2004, 6, 4223; Alam, M. S. et al. *J. Agricultural and Food Chemistry* 2006, 54, 1361; Pagliai, F. et al. *J. Med. Chem.* 2006, 49, 467.)

Scheme 5:

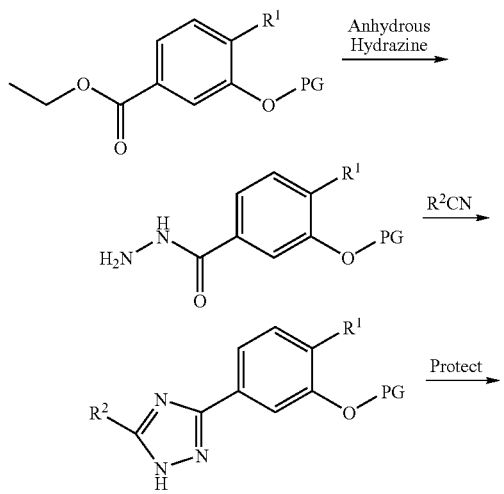

-continued

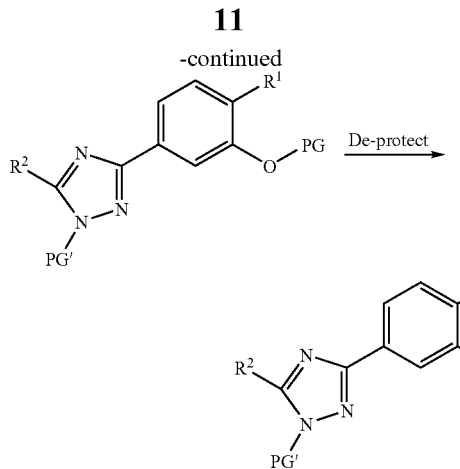

Synthesis of 1,2,4-triazoles are well documented in literature. One such method is the direct coupling of an appropriate nitrile with the hydrazide (see e.g. Yeung, K.-S. et al. *Tetrahedron Letters* 2005, 26, 3429.)

Scheme 6:

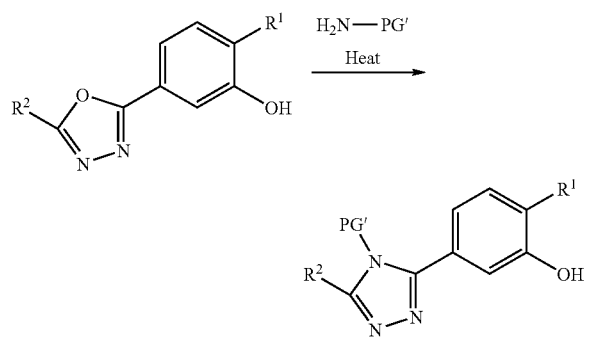

It is also well known in the art that oxadiazoles can be converted to the corresponding 1,2,4-triazoles by heating with the appropriate amine. See e.g. Reitz, D. B. et al. *J. Heterocyclic Chem.* 1989, 26, 225; Carlsen, P. H. J. et al. *J. Heterocyclic Chem.* 1994, 31, 805.

Scheme 7:

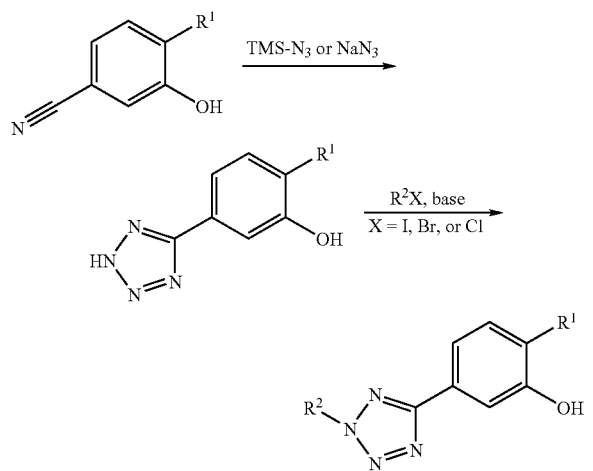

Scheme 8:

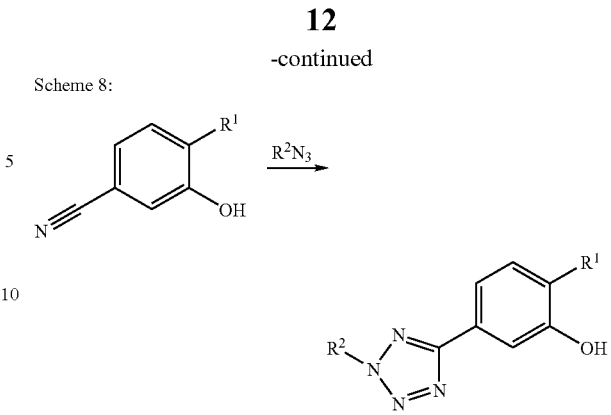

Reaction of nitriles with azides to give the corresponding tetrazoles are well know in the art. See e.g. Lukyanov, S. M. et al. *Tetrahedron* 2006, 62, 1849.

Scheme 9:

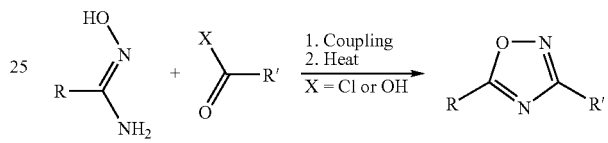

Formation of 1,2,4-oxadiazole is also well known in the art. One such method is acylating the appropriate amidoximes followed by cyclization by heating. (see e.g. Hamze, A. et al. *J. Org. Chem.* 2003, 68, 7316; Pipik, B. et al. *Synthetic Communications* 2004, 34, 1863, and references cited therein.)

The 3-bromomethyl-4-chloro-thieno[3,2-c]pyridine-7-carboxylic acid ethyl ester starting material was prepared as outlined in Scheme 10 from 3-methylthiophene (commercially available) according to the procedure of Luk, K.; McDermott, L. A.; Rossman, P. L.; Wovkulich, P. M.; Zhang, Z. US Patent 20050256154 A1.

Scheme 10:

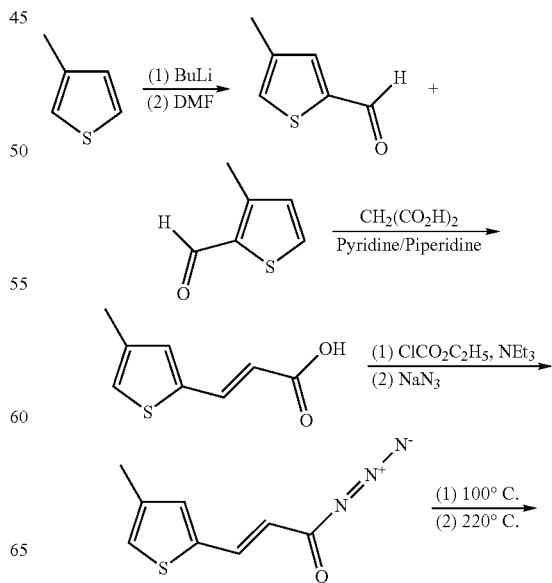

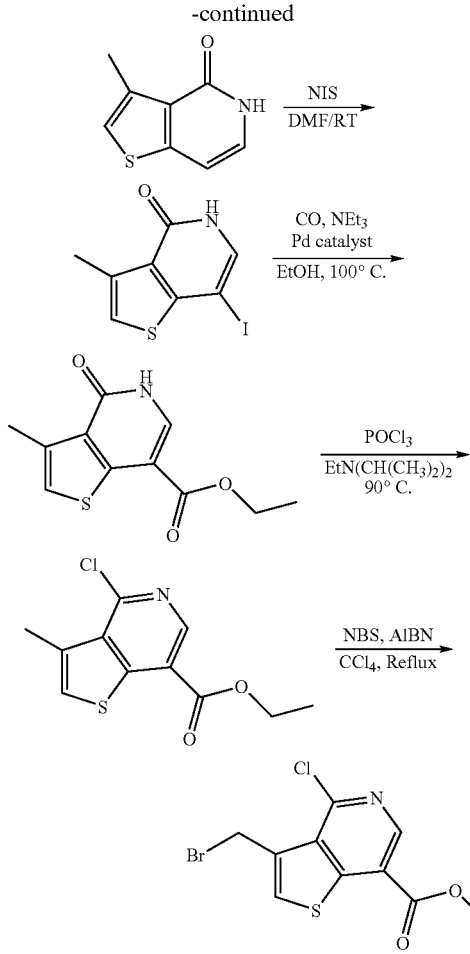

Scheme 11:

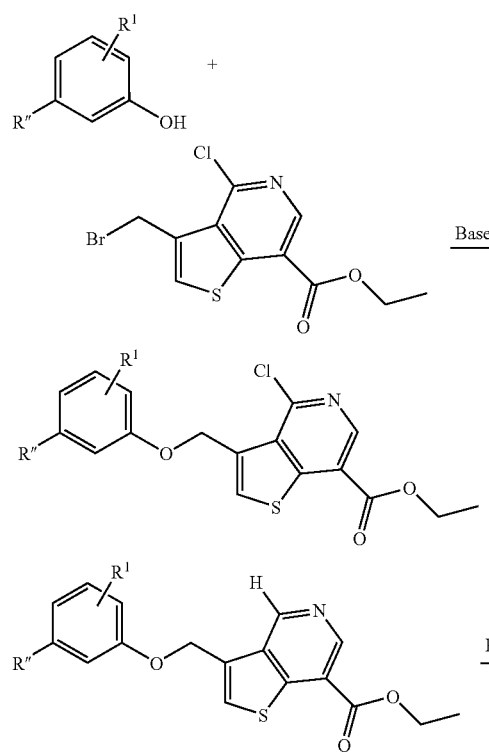

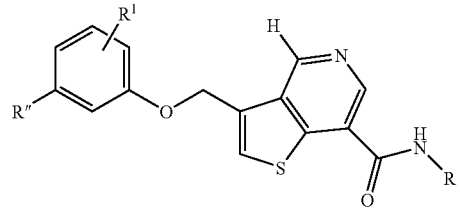

R″ is a group representing $R^2$—Ring B—[X—Y]—, or a group that with further chemical modification can be converted to $R^2$—Ring B—[X—Y]—. See e.g. Scheme 14 (in this case R″ is —$NO_2$).

As outlined in schemes 11 to 14, preparation of compounds of this invention can be achieved as follows. Coupling of an appropriate phenol (prepared for example by methods outlined in Schemes 1 to 9 supra) with 3-bromomethyl-4-chloro-thieno[3,2-c]pyridine-7-carboxylic acid ethyl ester (prepared according to Scheme 10 supra) in the presence of a base, such as potassium carbonate, cesium carbonate, or di-isopropyl ethylamine in a solvent such as DMF or THF at between −30° C. to heating at reflux of the solvent, usually between 30° C. to 80° C. produces the phenolic ether. These can be reduced, for example with a mixture of zinc and ammonium chloride in dioxane—DMF mixture at between −30° C. to heating at reflux of the solvent, usually at room temperature followed by standard procedures for converting ethyl esters to the appropriate amides to give the compounds of this invention.

Scheme 12:

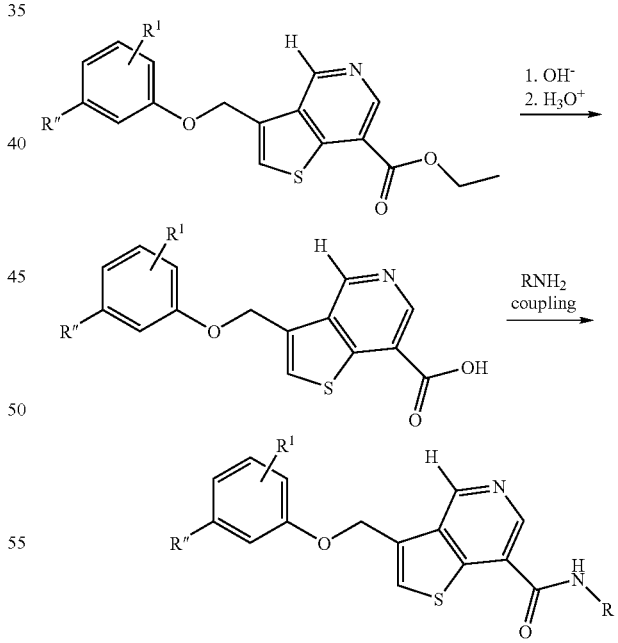

Scheme 13:

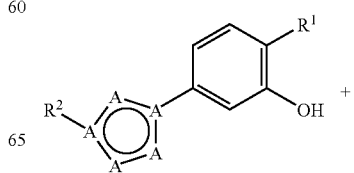

15
-continued
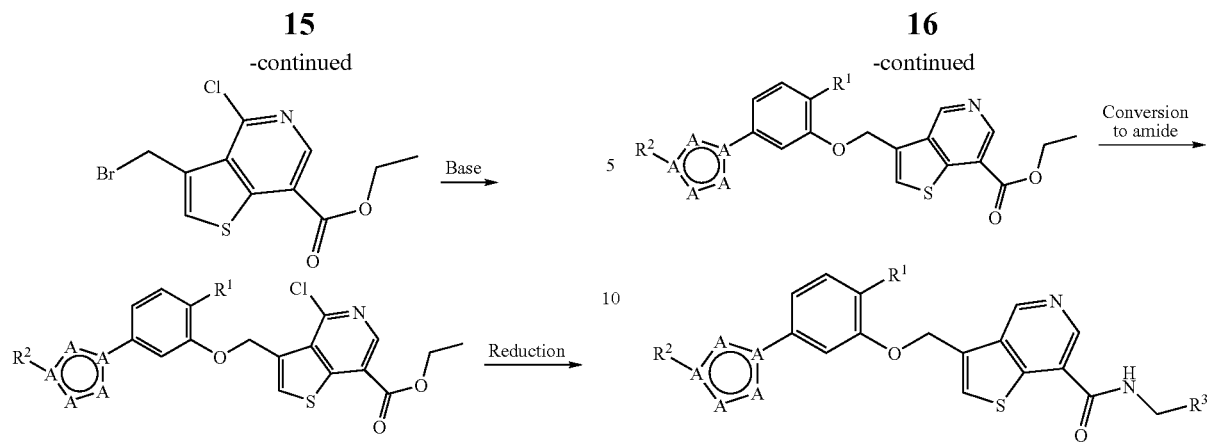
16
-continued
Scheme 14:
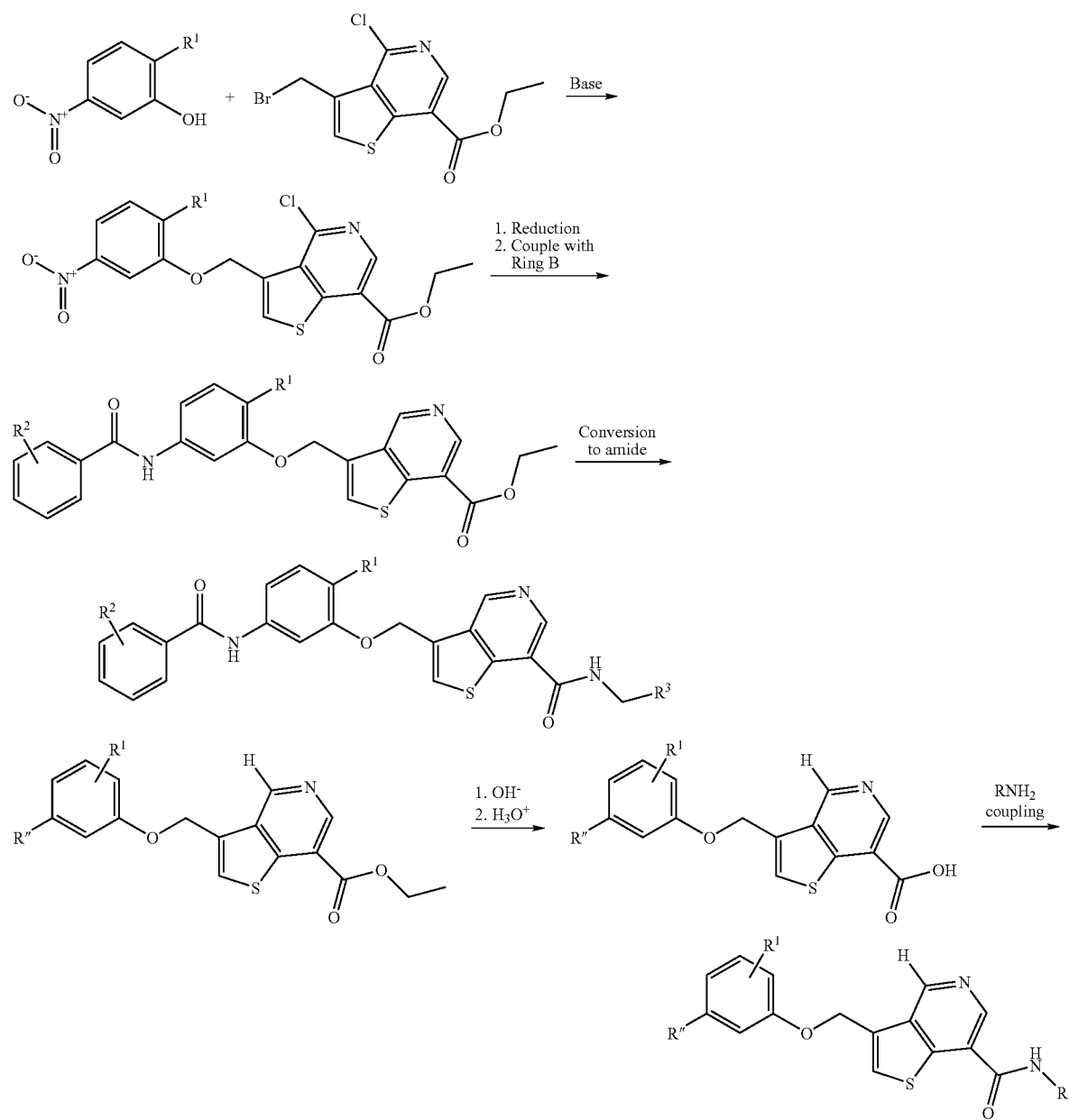

The following examples shall illustrate preferred embodiments of the present invention but are not intended to limit the scope of the invention.

Example 1

3-Bromomethyl-4-chloro-thieno[3,2-c]pyridine-7-carboxylic acid ethyl ester

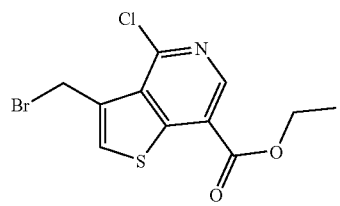

M.W. 334.62    $C_{11}H_9BrClNO_2S$

The 3-bromomethyl-4-chloro-thieno[3,2-c]pyridine-7-carboxylic acid ethyl ester starting material was prepared from 3-methylthiophene according to the procedure of Luk, K.; McDermott, L. A.; Rossman, P. L.; Wovkulich, P. M.; Zhang, Z. US Patent 20050256154 A1.

Example 2

4-Chloro-3-(3-nitro-phenoxymethyl)-thieno[3,2-c]pyridine-7-carboxylic acid ethyl ester

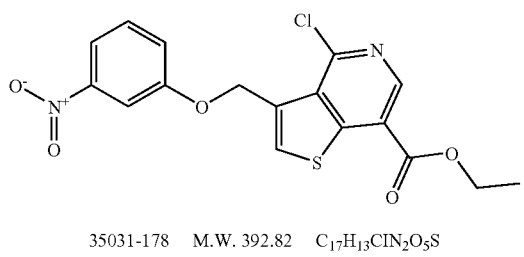

35031-178    M.W. 392.82    $C_{17}H_{13}ClN_2O_5S$

A mixture of 3-nitrophenol (457 mg, 3.29 mmol) (Aldrich) and potassium carbonate powder (498 mg, 3.60 mmol) in dry THF (10 mL) and DMF (5 mL) was stirred at 50° C. for 15 minutes before a solution of 3-bromomethyl-4-chloro-thieno[3,2-c]pyridine-7-carboxylic acid ethyl ester (1.00 g, 2.99 mmol) (from Example 1 supra) in THF (8+2 mL) was added. The reaction was stirred at 50° C. for 3 hours and the resulting mixture was concentrated to remove most of the solvent. The residue was dissolved in EtOAc (200 mL), washed with water (2×25 mL) and brine (25 mL), dried over $Na_2SO_4$ and concentrated. The crude product was purified by column chromatography ($CH_2Cl_2$/MeOH, 98/2 to 90/10) to give 4-chloro-3-(3-nitro-phenoxymethyl)-thieno[3,2-c]pyridine-7-carboxylic acid ethyl ester as a white solid. (Yield 911 mg, 78%).

HRMS (ES$^+$) m/z Calcd for $C_{17}H_{13}ClN_2O_5S$+H [(M+H)$^+$]: 393.0307. Found: 393.0308.

Example 3

3-(3-Amino-phenoxymethyl)-thieno[3,2-c]pyridine-7-carboxylic acid ethyl ester

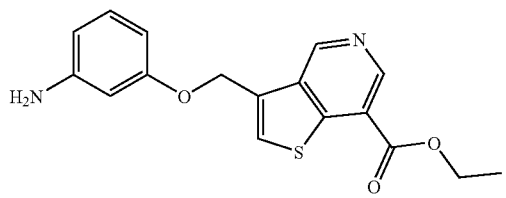

37304-86    M.W. 328.39    $C_{17}H_{16}N_2O_3S$

To a stirred solution of 4-chloro-3-(3-nitro-phenoxymethyl)-thieno[3,2-c]pyridine-7-carboxylic acid ethyl ester (398 mg, 1.01 mmol) (from Example 2 supra) in 1,4-dioxane (20 mL), THF (10 mL) and DMF (10 mL) was added $NH_4Cl$ (810 mg, 15.14 mmol) in water (6 mL). Zinc powder (783 mg, 12 mmol) was then added in several portions and the reaction was stirred at room temperature for a total of 4 hours. The resulting mixture was diluted with ethyl acetate (800 mL), washed with water (100 mL) and then brine (100 mL), dried ($Na_2SO_4$) and concentrated. The residue was purified by column chromatography (hexanes/EtOAc, 60/40 to 30/70) to give 3-(3-amino-phenoxymethyl)-thieno[3,2-c]pyridine-7-carboxylic acid ethyl ester as a white solid. (Yield 339.1 mg, 100%).

HRMS (ES$^+$) m/z Calcd for $C_{17}H_{16}N_2O_3S$+H [(M+H)$^+$]: 329.0955. Found: 329.0953.

Example 4

3-[3-(4-Chloro-benzoylamino)-phenoxymethyl]-thieno[3,2-c]pyridine-7-carboxylic acid ethyl ester

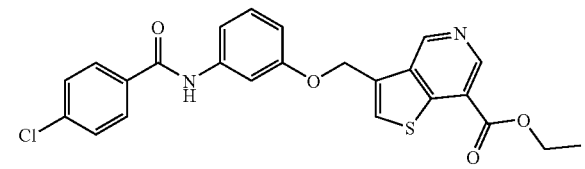

M.W. 466.947    $C_{24}H_{19}ClN_2O_4S$

To a solution of 3-(3-amino-phenoxymethyl)-thieno[3,2-c]pyridine-7-carboxylic acid ethyl ester (52 mg, 0.158 mmol) (from Example 3 supra) in THF (3 mL) were added diisopropylethylamine (44 mg, 0.35 mmol) and then 4-chlorobenzoyl chloride (30.8 mg, 0.174 mmol) (Aldrich). The reaction was stirred at room temperature for 30 minutes before it was concentrated to remove the solvent. The residue was diluted with EtOAc (50 mL), washed with aqueous 1N NaOH (10 mL), brine (2×10 mL), dried ($Na_2SO_4$) and concentrated. The residue was purified by column chromatography ($CH_2Cl_2$/MeOH, 99/1 to 95/5) to give 3-[3-(4-Chloro-benzoylamino)-phenoxymethyl]-thieno[3,2-c]pyridine-7-carboxylic acid ethyl ester as a white solid. (Yield 41.4 mg, 56%).

HRMS (ES$^+$) m/z Calcd for $C_{24}H_{19}ClN_2O_4S$+H [(M+H)$^+$]: 467.0827. Found: 467.0829.

Example 5

3-[3-(4-Chloro-benzoylamino)-phenoxymethyl]-thieno[3,2-c]pyridine-7-carboxylic acid (2-hydroxy-ethyl)-amide

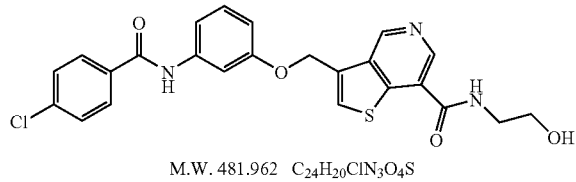

M.W. 481.962    $C_{24}H_{20}ClN_3O_4S$

A suspension of 3-[3-(4-chloro-benzoylamino)-phenoxymethyl]-thieno[3,2-c]pyridine-7-carboxylic acid ethyl ester (30 mg, 0.064 mmol) (from Example 4 supra) in methyl sulfoxide (1 mL) and ethanolamine (3 mL) (Aldrich) was heated at 135° C. for 2 hours in a microwave reactor. After cooling to room temperature, the precipitate was filtered off, washed with MeOH and dried to give 3-[3-(4-chloro-benzoylamino)-phenoxymethyl]-thieno[3,2-c]pyridine-7-carboxylic acid (2-hydroxy-ethyl)amide as a white solid. (Yield 13.2 mg, 42.6%).

HRMS (ES⁺) m/z Calcd for $C_{24}H_{20}ClN_3O_4S+H$ $[(M+H)^+]$: 482.0936. Found: 482.0937.

Example 6

3-(3-Benzoylamino-phenoxymethyl)-thieno[3,2-c]pyridine-7-carboxylic acid ethyl ester

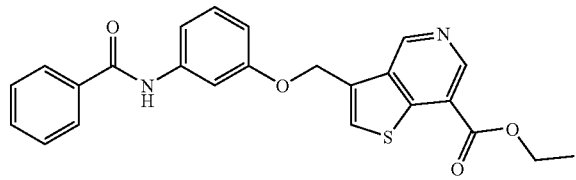

37304-087A    M.W. 432.502    $C_{24}H_{20}N_2O_4S$

To a solution of 3-(3-amino-phenoxymethyl)-thieno[3,2-c]pyridine-7-carboxylic acid ethyl ester (25.6 mg, 0.078 mmol) (from Example 3 supra) in THF (2 mL) were added diisopropylethyl-amine (22 mg, 0.170 mmol) (Aldrich) and then benzoyl chloride (12.5 mg, 0.085 mmol) (Aldrich). The reaction was stirred at room temperature for 30 minutes before it was concentrated to remove the solvent. The residue was diluted with EtOAc (40 mL), washed with aqueous 1N NaOH (10 mL), brine (2×10 mL), dried (Na₂SO₄) and concentrated. The residue was purified by column chromatography (hexanes/EtOAc, 60/40) to give 3-(3-benzoylamino-phenoxy-methyl)-thieno[3,2-c]pyridine-7-carboxylic acid ethyl ester as a white solid. (Yield 26.0 mg, 77%).

HRMS (ES⁺) m/z Calcd for $C_{24}H_{20}N_2O_4S+H$ $[(M+H)^+]$: 433.1217. Found: 433.1214.

Example 7

3-(3-Benzoylamino-phenoxymethyl)-thieno[3,2-c]pyridine-7-carboxylic acid (2-hydroxy-ethyl)-amide

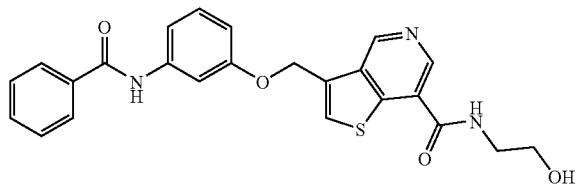

37304-089A    M.W. 447.517    $C_{24}H_{21}N_3O_4S$

A suspension of 3-(3-benzoylamino-phenoxymethyl)-thieno[3,2-c]pyridine-7-carboxylic acid ethyl ester (23.9 mg, 0.055 mmol) (from Example 3 supra) in methyl sulfoxide (0.5 mL) and ethanolamine (1.5 mL) (Aldrich) was heated at 135° C. for 2 hours in a microwave reactor. The solvent was removed in vacuum and the crude product was purified by column chromatography (CH₂Cl₂/MeOH, 98/2 to 90/10) to give 3-(3-benzoyl-amino-phenoxymethyl)-thieno[3,2-c]pyridine-7-carboxylic acid (2-hydroxy-ethyl)-amide as an off-white solid. (Yield 20.4 mg, 83%).

HRMS (ES⁺) m/z Calcd for $C_{24}H_{21}N_3O_4S+H$ $[(M+H)^+]$: 448.1326. Found: 448.1324.

Example 8

3-[3-(4-Fluoro-benzoylamino)-phenoxymethyl]-thieno[3,2-c]pyridine-7-carboxylic acid ethyl ester

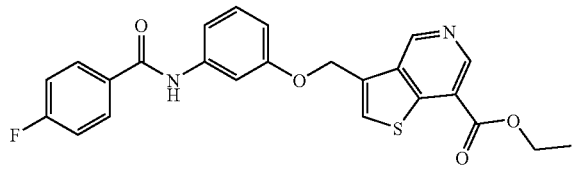

M.W. 450.492    $C_{24}H_{19}FN_2O_4S$

To a solution of 3-(3-amino-phenoxymethyl)-thieno[3,2-c]pyridine-7-carboxylic acid ethyl ester (25.6 mg, 0.078 mmol) (from Example 3 supra) in THF (2 mL) were added diisopropylethyl-amine (22 mg, 0.170 mmol) (Aldrich) and then 4-fluorobenzoyl chloride (13.4 mg, 0.085 mmol) (Aldrich). The reaction was stirred at room temperature for 30 minutes before it was concentrated to remove the solvent. The residue was diluted with EtOAc (40 mL), washed with aqueous 1N NaOH (10 mL), brine (2×10 mL), dried (Na₂SO₄) and concentrated. The residue was purified by column chromatography (hexanes/EtOAc, 70/30) to give 3-[3-(4-fluoro-benzoylamino)-phenoxymethyl]-thieno[3,2-c]pyridine-7-carboxylic acid ethyl ester as a white solid. (Yield 29 mg, 82.5%).

HRMS (ES⁺) m/z Calcd for $C_{24}H_{19}FN_2O_4S+H$ $[(M+H)^+]$: 451.1123. Found: 451.1119.

Example 9A

3-[3-(4-Fluoro-benzoylamino)-phenoxymethyl]-thieno[3,2-c]pyridine-7-carboxylic acid (2-hydroxy-ethyl)-amide

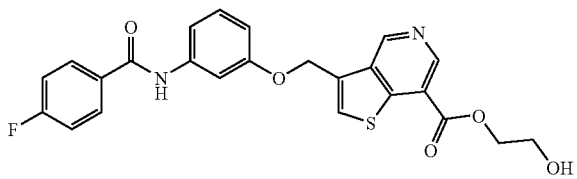

M.W. 465.507    $C_{24}H_{20}FN_3O_4S$

A suspension of 3-[3-(4-fluoro-benzoylamino)-phenoxymethyl]-thieno[3,2-c]pyridine-7-carboxylic acid ethyl ester (25.1 mg, 0.056 mmol) (from Example 8 supra) in methyl sulfoxide (0.5 mL) and ethanolamine (1.5 mL) (Aldrich) was heated at 135° C. for 2 hours in a microwave reactor. The solvent was removed in vacuum and the crude product was purified by column chromatography (CH₂Cl₂/MeOH, 98/2 to 80/20) to give two products. The faster eluting material gave 3-[3-(4-fluoro-benzoylamino)-phenoxymethyl]-thieno[3,2-c]pyridine-7-carboxylic acid (2-hydroxy-ethyl)-amide as a white solid. (Yield 7.3 mg, 28%).

HRMS (ES⁺) m/z Calcd for $C_{24}H_{20}FN_3O_4S+H$ $[(M+H)^+]$: 466.1232. Found: 466.1228.

Example 9B

3-{3-[4-(2-Hydroxy-ethylamino)-benzoylamino]-phenoxymethyl}-thieno[3,2-c]pyridine-7-carboxylic acid (2-hydroxy-ethyl)-amide

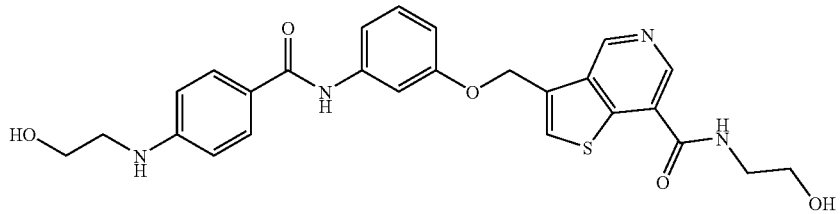

M.W. 506.585   $C_{26}H_{26}N_4O_5S$

The slower eluting material (from Example 9A supra) gave 3-{3-[4-(2-hydroxy-ethylamino)-benzoylamino]-phenoxymethyl}-thieno[3,2-c]pyridine-7-carboxylic acid (2-hydroxy-ethyl)-amide as a white solid. (Yield 14.1 mg, 50%).

HRMS (ES$^+$) m/z Calcd for $C_{26}H_{26}N_4O_5S$+H [(M+H)$^+$]: 507.1697. Found: 507.1697.

Example 10

3-[3-(3-Chloro-benzoylamino)-phenoxymethyl]-thieno[3,2-c]pyridine-7-carboxylic acid ethyl ester

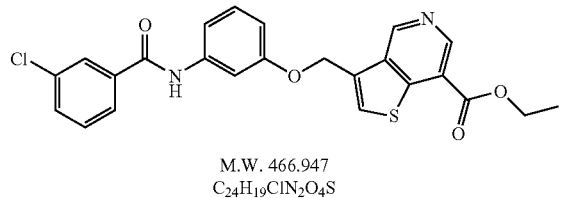

M.W. 466.947
$C_{24}H_{19}ClN_2O_4S$

To a solution of 3-(3-amino-phenoxymethyl)-thieno[3,2-c]pyridine-7-carboxylic acid ethyl ester (35.4 mg, 0.108 mmol) (from Example 3 supra) in THF (3 mL) were added diisopropylethyl-amine (28 mg, 0.216 mmol) (Aldrich) and then 3-chlorobenzoyl chloride (28 mg, 0.161 mmol) (Aldrich). The reaction was stirred at room temperature for 20 minutes before it was concentrated to remove the solvent. The residue was diluted with EtOAc (40 mL), washed with aqueous 1N NaOH (10 mL), brine (2×10 mL), dried (Na$_2$SO$_4$) and concentrated. The residue was purified by column chromatography (hexanes/EtOAc, 75/25 to 50/50) to give 3-[3-(3-chloro-benzoylamino)-phenoxymethyl]-thieno[3,2-c]pyridine-7-carboxylic acid ethyl ester as a white solid. (Yield 38.2 mg, 75.7%).

HRMS (ES$^+$) m/z Calcd for $C_{24}H_{19}ClN_2O_4S$+H [(M+H)$^+$]: 467.0827. Found: 467.0826.

Example 11

3-[3-(2-Chloro-benzoylamino)-phenoxymethyl]-thieno[3,2-c]pyridine-7-carboxylic acid ethyl ester

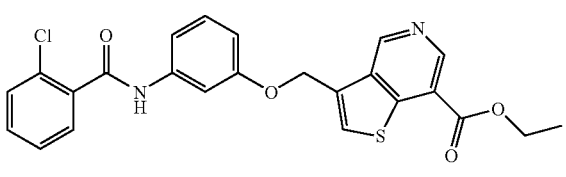

M.W. 466.947
$C_{24}H_{19}ClN_2O_4S$

3-[3-(2-Chloro-benzoylamino)-phenoxymethyl]-thieno[3,2-c]pyridine-7-carboxylic acid ethyl ester was prepared from 3-(3-amino-phenoxymethyl)-thieno[3,2-c]pyridine-7-carboxylic acid ethyl ester (from Example 3 supra) and 2-chlorobenzoyl chloride (Aldrich) following the procedure described in Example 10 as an off-white solid.

HRMS (ES$^+$) m/z Calcd for $C_{24}H_{19}ClN_2O_4S$+H [(M+H)$^+$]: 467.0827. Found: 467.0823.

Example 12

3-[3-(2-Fluoro-benzoylamino)-phenoxymethyl]-thieno[3,2-c]pyridine-7-carboxylic acid ethyl ester

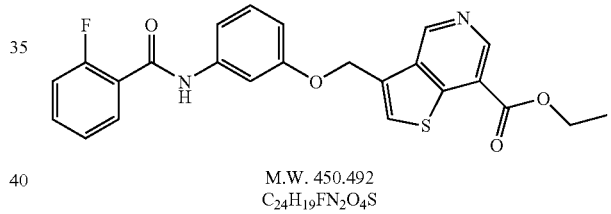

M.W. 450.492
$C_{24}H_{19}FN_2O_4S$

3-[3-(2-Fluoro-benzoylamino)-phenoxymethyl]-thieno[3,2-c]pyridine-7-carboxylic acid ethyl ester was prepared from 3-(3-amino-phenoxymethyl)-thieno[3,2-c]pyridine-7-carboxylic acid ethyl ester (from Example 3 supra) and 2-fluorobenzoyl chloride (Aldrich) following the procedure described in Example 10 as a white solid.

HRMS (ES$^+$) m/z Calcd for $C_{24}H_{19}FN_2O_4S$+H [(M+H)$^+$]: 451.1123. Found: 451.1119.

Example 13

3-[3-(3-Methoxy-benzoylamino)-phenoxymethyl]-thieno[3,2-c]pyridine-7-carboxylic acid ethyl ester

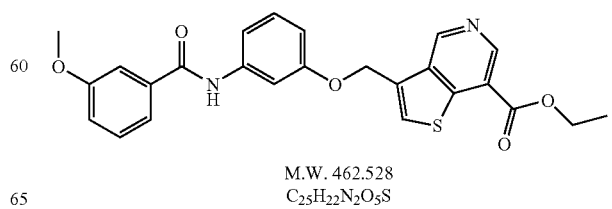

M.W. 462.528
$C_{25}H_{22}N_2O_5S$

3-[3-(3-Methoxy-benzoylamino)-phenoxymethyl]-thieno[3,2-c]pyridine-7-carboxylic acid ethyl ester was prepared from 3-(3-amino-phenoxymethyl)-thieno[3,2-c]pyridine-7-carboxylic acid ethyl ester (from Example 3 supra) and m-anisoyl chloride (Aldrich) following the procedure described in Example 10 as an off-white solid.

HRMS (ES+) m/z Calcd for $C_{25}H_{22}N_2O_5S$+H [(M+H)+]: 463.1322. Found: 463.1319.

Example 14

3-[3-(2-Methoxy-benzoylamino)-phenoxymethyl]-thieno[3,2-c]pyridine-7-carboxylic acid ethyl ester

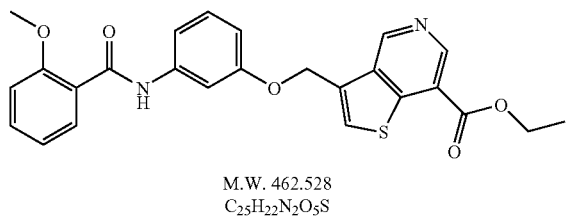

M.W. 462.528
$C_{25}H_{22}N_2O_5S$

3-[3-(2-Methoxy-benzoylamino)-phenoxymethyl]-thieno[3,2-c]pyridine-7-carboxylic acid ethyl ester was prepared from 3-(3-amino-phenoxymethyl)-thieno[3,2-c]pyridine-7-carboxylic acid ethyl ester (from Example 3 supra) and o-anisoyl chloride (Aldrich) following the procedure described in Example 10 as an off-white solid.

HRMS (ES+) m/z Calcd for $C_{25}H_{22}N_2O_5S$+H [(M+H)+]: 463.1322. Found: 463.1319.

Example 15

3-[3-(4-Methoxy-benzoylamino)-phenoxymethyl]-thieno[3,2-c]pyridine-7-carboxylic acid ethyl ester

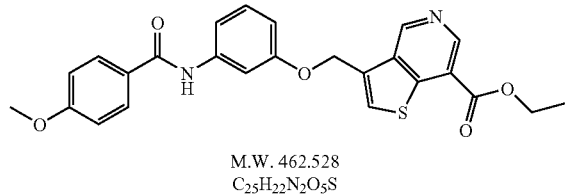

M.W. 462.528
$C_{25}H_{22}N_2O_5S$

3-[3-(4-Methoxy-benzoylamino)-phenoxymethyl]-thieno[3,2-c]pyridine-7-carboxylic acid ethyl ester was prepared from 3-(3-amino-phenoxymethyl)-thieno[3,2-c]pyridine-7-carboxylic acid ethyl ester (from Example 3 supra) and p-anisoyl chloride (Aldrich) following the procedure described in Example 10 as an off-white solid.

HRMS (ES+) m/z Calcd for $C_{25}H_{22}N_2O_5S$+H [(M+H)+]: 463.1322. Found: 463.1325.

Example 16

3-[3-(3-Chloro-benzoylamino)-phenoxymethyl]-thieno[3,2-c]pyridine-7-carboxylic acid (2-hydroxy-ethyl)-amide

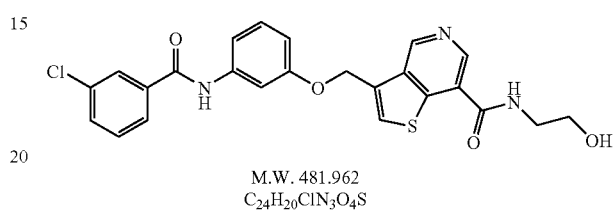

M.W. 481.962
$C_{24}H_{20}ClN_3O_4S$

A suspension of 3-[3-(3-chloro-benzoylamino)-phenoxymethyl]-thieno[3,2-c]pyridine-7-carboxylic acid ethyl ester (34.0 mg, 0.073 mmol) (from Example 10 supra) in methyl sulfoxide (1 mL) and ethanolamine (3 mL) (Aldrich) was heated at 135° C. for 2 hours in a microwave reactor. The solvent was removed in vacuum and the residue was treated with MeOH (2 mL). The resulting white precipitate was filtered, washed with cold MeOH and dried to give 3-[3-(3-chloro-benzoylamino)-phenoxymethyl]-thieno[3,2-c]pyridine-7-carboxylic acid (2-hydroxy-ethyl)-amide as a white solid. (Yield 25.7 mg, 73%).

HRMS (ES+) m/z Calcd for $C_{24}H_{20}ClN_3O_4S$+H [(M+H)+]: 482.0936. Found: 482.0936.

Example 17

3-[3-(2-Chloro-benzoylamino)-phenoxymethyl]-thieno[3,2-c]pyridine-7-carboxylic acid (2-hydroxy-ethyl)-amide

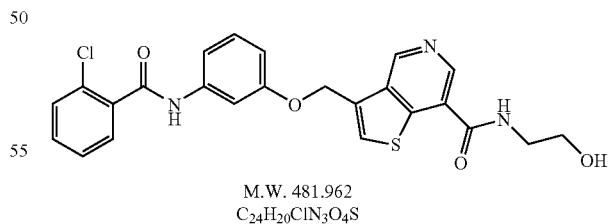

M.W. 481.962
$C_{24}H_{20}ClN_3O_4S$

3-[3-(2-Chloro-benzoylamino)-phenoxymethyl]-thieno[3,2-c]pyridine-7-carboxylic acid (2-hydroxy-ethyl)-amide was prepared from 3-[3-(2-chloro-benzoylamino)-phenoxymethyl]-thieno[3,2-c]pyridine-7-carboxylic acid ethyl ester (from Example 11 supra) and ethanolamine (Aldrich) following the procedure described in Example 16 as a light-yellow solid.

HRMS (ES+) m/z Calcd for $C_{24}H_{20}ClN_3O_4S$+H [(M+H)+]: 482.0936. Found: 482.0937.

Example 18

3-[3-(2-Fluoro-benzoylamino)-phenoxymethyl]-thieno[3,2-c]pyridine-7-carboxylic acid (2-hydroxy-ethyl)-amide

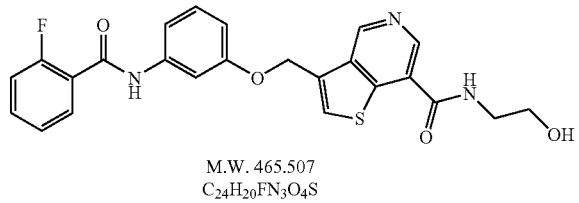

M.W. 465.507
$C_{24}H_{20}FN_3O_4S$

3-[3-(2-Fluoro-benzoylamino)-phenoxymethyl]-thieno[3,2-c]pyridine-7-carboxylic acid (2-hydroxy-ethyl)-amide was prepared from 3-[3-(2-fluoro-benzoylamino)-phenoxymethyl]-thieno[3,2-c]pyridine-7-carboxylic acid ethyl ester (from Example 12 supra) and ethanolamine (Aldrich) following the procedure described in Example 16 as a white solid.

HRMS (ES+) m/z Calcd for $C_{24}H_{20}FN_3O_4S$+H [(M+H)+]: 466.1232. Found: 466.1227.

Example 19

3-[3-(3-Methoxy-benzoylamino)-phenoxymethyl]-thieno[3,2-c]pyridine-7-carboxylic acid (2-hydroxy-ethyl)-amide

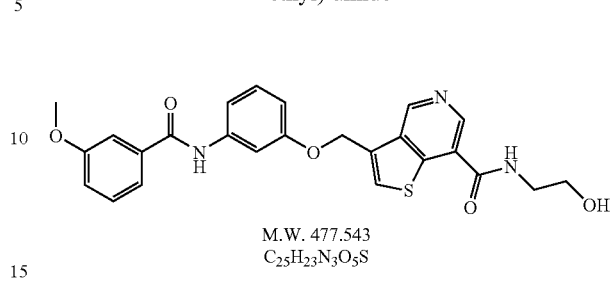

M.W. 477.543
$C_{25}H_{23}N_3O_5S$

3-[3-(3-Methoxy-benzoylamino)-phenoxymethyl]-thieno[3,2-c]pyridine-7-carboxylic acid (2-hydroxy-ethyl)-amide was prepared from 3-[3-(3-methoxy-benzoylamino)-phenoxymethyl]-thieno[3,2-c]pyridine-7-carboxylic acid ethyl ester (from Example 13 supra) and ethanolamine (Aldrich) following the procedure described in Example 16 as a white solid.

HRMS (ES+) m/z Calcd for $C_{25}H_{23}N_3O_5S$+H [(M+H)+]: 478.1431. Found: 478.1426.

Example 20

3-[3-(4-Methoxy-benzoylamino)-phenoxymethyl]-thieno[3,2-c]pyridine-7-carboxylic acid (2-hydroxy-ethyl)-amide

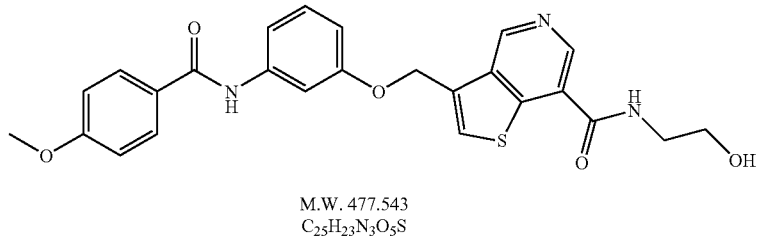

M.W. 477.543
$C_{25}H_{23}N_3O_5S$

3-[3-(4-Methoxy-benzoylamino)-phenoxymethyl]-thieno[3,2-c]pyridine-7-carboxylic acid (2-hydroxy-ethyl)-amide was prepared from 3-[3-(4-methoxy-benzoylamino)-phenoxymethyl]-thieno[3,2-c]pyridine-7-carboxylic acid ethyl ester (from Example 15 supra) and ethanolamine (Aldrich) following the procedure described in Example 16 as a white solid.

HRMS (ES+) m/z Calcd for $C_{25}H_{23}N_3O_5S$+H [(M+H)+]: 478.1431. Found: 478.1427.

Example 21

3-[3-(2-Hydroxy-benzoylamino)-phenoxymethyl]-thieno[3,2-c]pyridine-7-carboxylic acid (2-hydroxy-ethyl)-amide

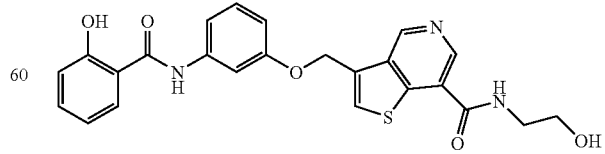

M.W. 463.516
$C_{24}H_{21}N_3O_5S$

A suspension of 3-[3-(2-methoxy-benzoylamino)-phenoxymethyl]-thieno[3,2-c]pyridine-7-carboxylic acid ethyl ester (28.0 mg, 0.061 mmol) (from Example 14 supra) in methyl sulfoxide (1 mL) and ethanolamine (3 mL) (Aldrich) was heated at 135° C. for 2 hours in a microwave reactor. The solvent was removed in vacuum and the residue was treated with MeOH (2 mL). The resulting white precipitate was filtered, washed with cold MeOH and dried to give 3-[3-(2-hydroxy-benzoylamino)-phenoxymethyl]-thieno[3,2-c]pyridine-7-carboxylic acid (2-hydroxy-ethyl)-amide as a white solid. (Yield 7 mg, 25%).

HRMS (ES$^+$) m/z Calcd for $C_{24}H_{21}N_3O_5S$+H [(M+H)$^+$]: 464.1275. Found: 464.1274.

Example 22

4-Chloro-3-(2-methyl-5-nitro-phenoxymethyl)-thieno[3,2-c]pyridine-7-carboxylic acid ethyl ester

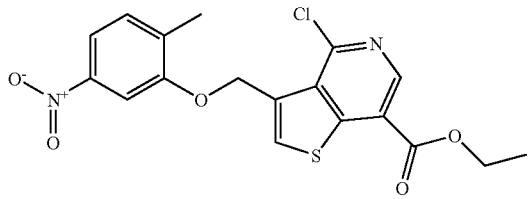

M.W. 406.848
$C_{18}H_{15}ClN_2O_5S$

A mixture of 2-methyl-5-nitrophenol (960 mg, 6.07 mmol) (Avocado) and potassium carbonate powder (913 mg, 6.61 mmol) in dry THF (20 mL) and DMF (10 mL) was stirred at 50° C. for 15 minutes before a solution of 3-bromomethyl-4-chloro-thieno[3,2-c]pyridine-7-carboxylic acid ethyl ester (1.997 g, 5.969 mmol) (from Example 1 supra) in THF (20 mL) was added. The reaction was stirred at 50° C. for 10 hours and the resulting precipitate was collected. The filtrate was concentrated to give more precipitate. The combined solid was stirred in water (30 mL), filtered, washed with water and dried overnight to give 4-chloro-3-(2-methyl-5-nitro-phenoxymethyl)-thieno[3,2-c]pyridine-7-carboxylic acid ethyl ester as a white solid. (Yield 1.647 g, 68%).

LRMS (ES$^+$) m/z Calcd for $C_{18}H_{15}ClN_2O_5S$+H [(M+H)$^+$]: 407. Found: 407.

Example 23

3-(5-Amino-2-methyl-phenoxymethyl)-thieno[3,2-c]pyridine-7-carboxylic acid ethyl ester

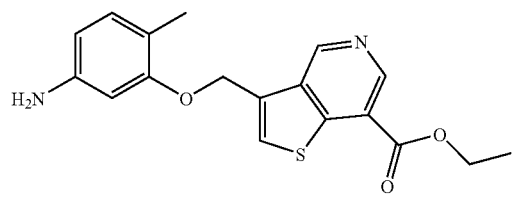

M.W. 342.420
$C_{18}H_{18}N_2O_3S$

To a stirred solution of 4-chloro-3-(2-methyl-5-nitro-phenoxymethyl)-thieno[3,2-c]pyridine-7-carboxylic acid ethyl ester (815.2 mg, 2.00 mmol) (from Example 22 supra) in 1,4-dioxane (40 mL), THF (20 mL) and DMF (20 mL) was added NH$_4$Cl (1.59 mg, 29.6 mmol) in water (12 mL). Zinc powder (948 mg, 14.5 mmol) was then added in several portions and the reaction was stirred at room temperature for a total of 4 hours. The resulting mixture was diluted with ethyl acetate (800 mL), washed with water (100 mL) and then brine (100 mL), dried (Na$_2$SO$_4$) and concentrated. The residue was purified by column chromatography (CH$_2$Cl$_2$/MeOH, 98/2 to 95/5) to give 3-(5-amino-2-methyl-phenoxymethyl)-thieno[3,2-c]pyridine-7-carboxylic acid ethyl ester as a white solid. (Yield 584 mg, 85%).

HRMS (ES$^+$) m/z Calcd for $C_{18}H_{18}N_2O_3S$+H [(M+H)$^+$]: 343.1111. Found: 343.1109.

Example 24

3-[5-(3-Chloro-benzoylamino)-2-methyl-phenoxymethyl]-thieno[3,2-c]pyridine-7-carboxylic acid ethyl ester

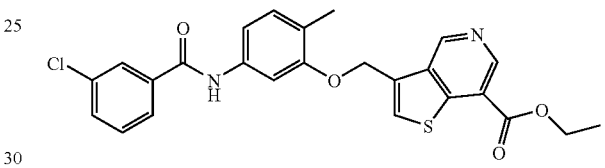

M.W. 480.974
$C_{25}H_{21}ClN_2O_4S$

To a solution of 3-(5-amino-2-methyl-phenoxymethyl)-thieno[3,2-c]pyridine-7-carboxylic acid ethyl ester (346.7 mg, 1.01 mmol) (from Example 23 supra) in THF (20 mL) were added diisopropylethylamine (258 mg, 2.03 mmol) (Aldrich) and then 3-chlorobenzoyl chloride (265 mg, 1.51 mmol) (Aldrich). The reaction was stirred at room temperature for 30 minutes before it was concentrated to remove the solvent. The residue was diluted with EtOAc (200 mL), washed with aqueous 1N NaOH (15 mL), brine (2×15 mL), dried (Na$_2$SO$_4$) and concentrated. The residue was purified by column chromatography (CH$_2$Cl$_2$/MeOH, 99/1 to 95/5) to give 3-[5-(3-chloro-benzoylamino)-2-methyl-phenoxymethyl]-thieno[3,2-c]pyridine-7-carboxylic acid ethyl ester as a white solid. (Yield 468 mg, 97%).

HRMS (ES$^+$) m/z Calcd for $C_{25}H_{21}ClN_2O_4S$+H [(M+H)$^+$]: 481.0984. Found: 481.0979.

Example 25

3-[5-(3-Chloro-benzoylamino)-2-methyl-phenoxymethyl]-thieno[3,2-c]pyridine-7-carboxylic acid (2-hydroxy-ethyl)-amide

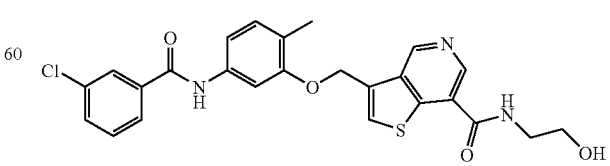

M.W. 495.989   $C_{25}H_{22}ClN_3O_4S$

A mixture of 3-[5-(3-chloro-benzoylamino)-2-methyl-phenoxymethyl]-thieno[3,2-c]pyridine-7-carboxylic acid ethyl ester (315 mg, 0.65 mmol) (from Example 24 supra) in methyl sulfoxide (3 mL) and ethanolamine (9 mL) (Aldrich) was heated at 135° C. for 2 hours in a microwave reactor. After cooling to room temperature, the precipitate was filtered off, washed thoroughly with MeOH and dried to give 3-[5-(3-chloro-benzoylamino)-2-methyl-phenoxymethyl]-thieno[3,2-c]pyridine-7-carboxylic acid (2-hydroxy-ethyl)-amide as a white solid. (Yield 267 mg, 82.8%).

HRMS (ES$^+$) m/z Calcd for $C_{25}H_{22}ClN_3O_4S+H$ [(M+H)$^+$]: 496.1093. Found: 496.1088.

Example 26

3-[5-(3-Chloro-benzoylamino)-2-methyl-phenoxymethyl]-thieno[3,2-c]pyridine-7-carboxylic acid (2-hydroxy-ethyl)-amide, toluene-4-sulfonic acid salt

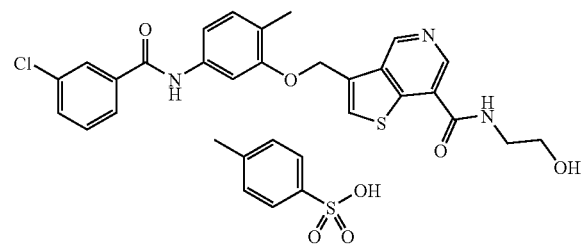

37009-225A    M.W. 495.989 + 172.204    $C_{25}H_{22}ClN_3O_4S \cdot C_7H_8O_3S$ To solution of 3-[5-(3-chloro-benzoylamino)-2-methyl-phenoxymethyl]-thieno[3,2-c]pyridine-7-carboxylic acid (2-hydroxy-ethyl)-amide (0.01 g, 0.02 mmol) (from Example 25 supra) in methanol (2 mL) was treated with toluene-4-sulfonic acid hydrate (10.0 mg, 0.05 mmol) (Aldrich) and heated at 40° C. for 30 minutes. The solution was concentrated. The residue was washed with diethyl ether, and then dissolved in water and lyophilized to give 3-[5-(3-chloro-benzoylamino)-2-methyl-phenoxymethyl]-thieno[3,2-c]pyridine-7-carboxylic acid (2-hydroxy-ethyl)-amide, toluene-4-sulfonic acid salt. (Yield: 12.0 mg, 92%).

HRMS (ES$^+$) m/z Calcd for $C_{25}H_{22}ClN_3O_4S+H$ [(M+H)$^+$]: 496.1093. Found: 496.1090.

Example 27

3-[5-(3-Fluoro-benzoylamino)-2-methyl-phenoxymethyl]-thieno[3,2-c]pyridine-7-carboxylic acid ethyl ester

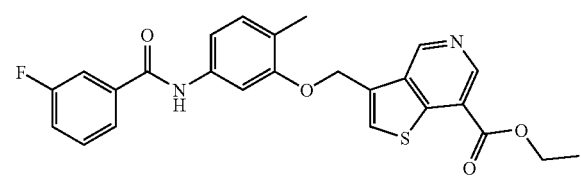

M.W. 464.520    $C_{25}H_{21}FN_2O_4S$

3-[5-(3-Fluoro-benzoylamino)-2-methyl-phenoxymethyl]-thieno[3,2-c]pyridine-7-carboxylic acid ethyl ester was prepared from 3-(5-amino-2-methyl-phenoxymethyl)-thieno[3,2-c]pyridine-7-carboxylic acid ethyl ester (from Example 23 supra) and 3-fluorobenzoyl chloride (Aldrich) following the procedure described in Example 10 as an off-white solid.

HRMS (ES$^+$) m/z Calcd for $C_{25}H_{21}FN_2O_4S+H$ [(M+H)$^+$]: 465.1279. Found: 465.1278.

Example 28

3-[5-(4-Fluoro-benzoylamino)-2-methyl-phenoxymethyl]-thieno[3,2-c]pyridine-7-carboxylic acid ethyl ester

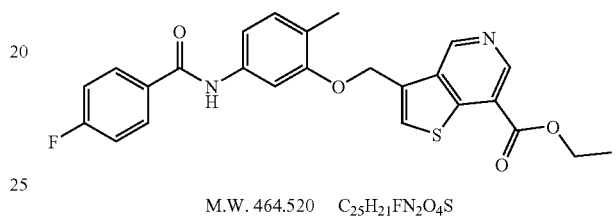

M.W. 464.520    $C_{25}H_{21}FN_2O_4S$

3-[5-(4-Fluoro-benzoylamino)-2-methyl-phenoxymethyl]-thieno[3,2-c]pyridine-7-carboxylic acid ethyl ester was prepared from 3-(5-amino-2-methyl-phenoxymethyl)-thieno[3,2-c]pyridine-7-carboxylic acid ethyl ester (from Example 23 supra) and 4-fluorobenzoyl chloride (Aldrich) following the procedure described in Example 10 as an off-white solid.

HRMS (ES$^+$) m/z Calcd for $C_{25}H_{21}FN_2O_4S+H$ [(M+H)$^+$]: 465.1279. Found: 465.1275.

Example 29

3-[5-(3-Methoxy-benzoylamino)-2-methyl-phenoxymethyl]-thieno[3,2-c]pyridine-7-carboxylic acid ethyl ester

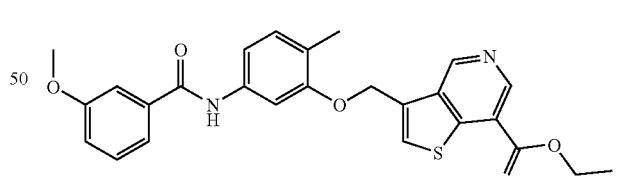

M.W. 476.556    $C_{26}H_{24}N_2O_5S$

3-[5-(3-Methoxy-benzoylamino)-2-methyl-phenoxymethyl]-thieno[3,2-c]pyridine-7-carboxylic acid ethyl ester was prepared from 3-(5-amino-2-methyl-phenoxymethyl)-thieno[3,2-c]pyridine-7-carboxylic acid ethyl ester (from Example 23 supra) and 3-anisoyl chloride (Aldrich) following the procedure described in Example 10 as an off-white solid.

HRMS (ES$^+$) m/z Calcd for $C_{26}H_{24}N_2O_5S+H$ [(M+H)$^+$]: 477.1479. Found: 477.1472.

Example 30

3-[5-(4-Fluoro-benzoylamino)-2-methyl-phenoxymethyl]-thieno[3,2-c]pyridine-7-carboxylic acid (2-hydroxy-ethyl)-amide

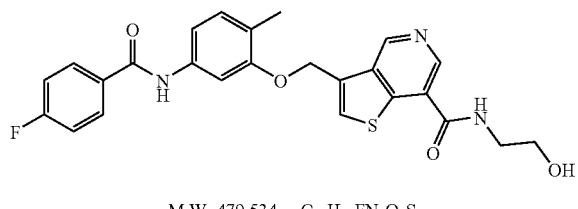

M.W. 479.534   $C_{25}H_{22}FN_3O_4S$

3-[5-(4-Fluoro-benzoylamino)-2-methyl-phenoxymethyl]-thieno[3,2-c]pyridine-7-carboxylic acid (2-hydroxyethyl)-amide was prepared from 3-[5-(4-fluoro-benzoylamino)-2-methyl-phenoxymethyl]-thieno[3,2-c]pyridine-7-carboxylic acid ethyl ester (from Example 28 supra) following the procedure described in Example 25 as an off-white solid.

HRMS (ES$^+$) m/z Calcd for $C_{25}H_{22}FN_3O_4S$+H [(M+H)$^+$]: 480.1388. Found: 480.1385.

Example 31

3-[5-(3-Methoxy-benzoylamino)-2-methyl-phenoxymethyl]-thieno[3,2-c]pyridine-7-carboxylic acid (2-hydroxy-ethyl)-amide

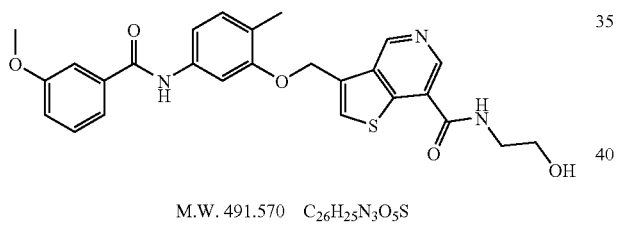

M.W. 491.570   $C_{26}H_{25}N_3O_5S$

3-[5-(3-Methoxy-benzoylamino)-2-methyl-phenoxymethyl]-thieno[3,2-c]pyridine-7-carboxylic acid (2-hydroxyethyl)-amide was prepared from 3-[5-(3-methoxy-benzoylamino)-2-methyl-phenoxymethyl]-thieno[3,2-c]pyridine-7-carboxylic acid ethyl ester (from Example 29 supra) following the procedure described in Example 25 as an off-white solid.

HRMS (ES$^+$) m/z Calcd for $C_{26}H_{25}N_3O_5S$+H [(M+H)$^+$]: 492.1588. Found: 492.1585.

Example 32

3-Hydroxy-4-methyl-benzoic acid ethyl ester

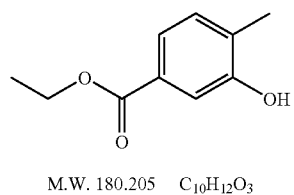

M.W. 180.205   $C_{10}H_{12}O_3$

A mixture of 3-hydroxy-4-methylbenzoic acid (25.42 g, 167 mmol) (TCI US) and concentrated sulfuric acid (3 mL) in absolute ethanol (180 mL) was heated at reflux for 20 hours. After cooling, solid sodium bicarbonate (10 g) was added to neutralize the acid. Mixture was partitioned between diethyl ether (2×400 mL) and water (2×300 mL). Organic layers were washed with brine (300 mL), combined, dried (MgSO$_4$), filtered, and concentrated. Residue was recrystallized from hexanes to give 3-hydroxy-4-methyl-benzoic acid ethyl ester as white crystals in two crops. (Yield 29.14 g, 96.8%).

Example 33

3-Hydroxy-4-methyl-benzoic acid hydrazide

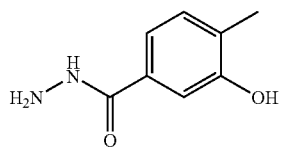

M.W. 166.181   $C_8H_{10}N_2O_2$

A suspension of ethyl 3-hydroxy-4-methylbenzoate (14.42 g, 80 mmol) (from Example 32 supra) in anhydrous hydrazine (30 mL, 956 mmol) (Aldrich) was heated at reflux (150° C. bath temperature) for 2.0 hours. After cooling to room temperature, mixture was concentrated under reduced pressure (high vacuum) to give crude 3-hydroxy-4-methyl-benzoic acid hydrazide as an off-white solid. (Yield 13.26 g, 100%).

Example 34

2-Methyl-5-(5-methyl-[1,3,4]oxadiazol-2-yl)-phenol

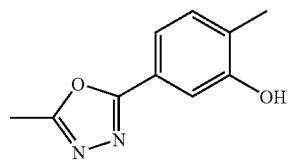

M.W. 190.203   $C_{10}H_{10}N_2O_2$

A suspension of ethyl 3-hydroxy-4-methylbenzoate (3.60 g, 20 mmol) (from Example 33 supra) in anhydrous hydrazine (10 mL, 318 mmol) (Aldrich) was heated at reflux (150° C. bath temperature) for 3 hours. After cooling to room temperature, mixture was concentrated under reduced pressure to give a dry solid. This was suspended in xylene (50 mL) and concentrated under reduced pressure. Resulting solid was suspended in triethyl ortho-acetate (35 mL, 191 mmol) (Aldrich) and heated at reflux (150° C. bath temperature) for 20 hours with removal of ethanol. After cooling, dichloromethane was added and solid was collected by filtration to give 2-methyl-5-(5-methyl-[1,3,4]oxadiazol-2-yl)-phenol as an off-white crystalline material. (Yield 2.28 g, 60.0%).

Filtrate from above was purified by flash chromatography (Biotage 40 L, 10% then 40% ethyl acetate in dichloromethane as solvent) to give second crop of 2-methyl-5-(5-methyl-[1,3,4]oxadiazol-2-yl)-phenol as a white crystalline material. (Yield 0.99 g, 26.0%).

Example 35

4-Chloro-3-[2-methyl-5-(5-methyl-[1,3,4]oxadiazol-2-yl)-phenoxymethyl]-thieno[3,2-c]pyridine-7-carboxylic acid ethyl ester

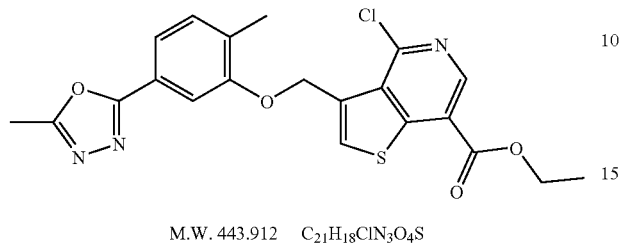

M.W. 443.912    $C_{21}H_{18}ClN_3O_4S$

A suspension of 3-bromomethyl-4-chloro-thieno[3,2-c]pyridine-7-carboxylic acid ethyl ester (0.29 g, 0.87 mmol) (from Example 1 supra), potassium iodide (0.14 g, 0.87 mmol), 2-methyl-5-(5-methyl-[1,3,4]oxadiazol-2-yl)-phenol (0.17 g, 0.9 mmol) (from Example 34 supra), potassium carbonate (0.27 g, 1.9 mmol) and 18-Crown-6 (10 mg, 0.04 mmol) (Aldrich) in N,N-dimethylformamide (5 mL) was heated at 65° C. in a sealed tube with magnetic stirring for 20 hours. After cooling, mixture was partitioned between ethyl acetate (2×100 mL) and water (2×100 mL). Aqueous layers were extracted with dichloromethane (2×100 mL). [Material was more soluble in dichloromethane than ethyl acetate.] Organic layers were washed with brine, then combined, dried ($MgSO_4$), filtered and concentrated. Residue was purified by flash chromatography (Biotage 40S, dichloromethane then 20% ethyl acetate in dichloromethane as solvent) to give 4-chloro-3-[2-methyl-5-(5-methyl-[1,3,4]oxadiazol-2-yl)-phenoxymethyl]-thieno[3,2-c]pyridine-7-carboxylic acid ethyl ester as a white powder. (Yield 0.24 g, 62.4%).

Example 36

3-[2-Methyl-5-(5-methyl-[1,3,4]oxadiazol-2-yl)-phenoxymethyl]-thieno[3,2-c]pyridine-7-carboxylic acid ethyl ester

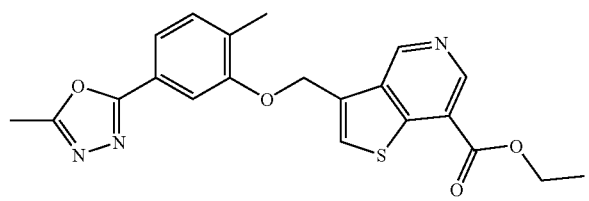

M.W. 409.467    $C_{21}H_{19}N_3O_4S$

To solution of 4-chloro-3-[2-methyl-5-(5-methyl-[1,3,4]oxadiazol-2-yl)-phenoxymethyl]-thieno[3,2-c]pyridine-7-carboxylic acid ethyl ester (0.11 g, 0.26 mmol) (from Example 35 supra) in methanol (10 mL) was treated with zinc (dust) (0.17 g, 2.60 mmol) and ammonium chloride (23.0 mg, 0.44 mmol). The mixture was heated at reflux for 18 hours. The solid was filtered off and the filtrate was concentrated. The residue from the filtrate was recrystallized from methanol to give a 1:1 mixture of 3-[2-methyl-5-(5-methyl-[1,3,4]oxadiazol-2-yl)-phenoxy-methyl]-thieno[3,2-c]pyridine-7-carboxylic acid ethyl ester and 3-[2-methyl-5-(5-methyl-[1,3,4]oxadiazol-2-yl)-phenoxymethyl]-thieno[3,2-c]pyridine-7-carboxylic acid methyl ester. (Yield 80.0 mg, 80%).

Example 37

3-{5-[4-(2-Hydroxy-ethyl)-5-methyl-4H-[1,2,4]triazol-3-yl]-2-methyl-phenoxymethyl}-thieno[3,2-c]pyridine-7-carboxylic acid (2-hydroxy-ethyl)-amide

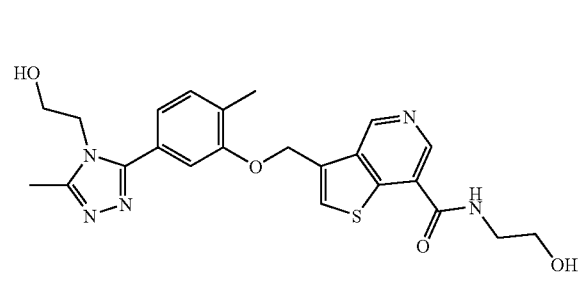

37009-150A    M.W. 467.551    $C_{23}H_{25}N_5O_4S$

A mixture of 3-[2-methyl-5-(5-methyl-[1,3,4]oxadiazol-2-yl)-phenoxymethyl]-thieno[3,2-c]pyridine-7-carboxylic acid ethyl ester and 3-[2-methyl-5-(5-methyl-[1,3,4]oxadiazol-2-yl)-phenoxymethyl]-thieno[3,2-c]pyridine-7-carboxylic acid methyl ester (0.08 g, 0.20 mmol) (from Example 36 supra) in dimethylsulfoxide (0.5 mL) was treated with ethanolamine (1.5 mL) (Aldrich) and heated at 160° C. for 2 hours in a microwave reactor. The reaction mixture was purified by C18 column chromatography eluting with acetonitrile/water to give 3-{5-[4-(2-hydroxy-ethyl)-5-methyl-4H-[1,2,4]triazol-3-yl]-2-methyl-phenoxymethyl}-thieno[3,2-c]pyridine-7-carboxylic acid (2-hydroxy-ethyl)-amide as a white solid. (Yield: 37.0 mg, 39%).

HRMS ($ES^+$) m/z Calcd for $C_{23}H_{25}N_5O_4S+H$ [$(M+H)^+$]: 468.1700. Found: 468.1697.

Example 38

Enzyme Assay

PDGFRβ IMAP Kinase Assay

Assay Principle:

The assay uses IMAP Fluorescence polarization (FP) assay platform based on the high affinity binding of phosphate by immobilized metal coordination complexes. The substrate used in this assay is a Fitc labeled peptide: FITC-ALTSN-QEYLDLSMPL. Upon substrate peptide's phosphorylation, the IMAP binding reagent complexes with phosphate groups on phosphopeptides generated in the PDGFRβ reaction, which causes a change in the rate of the molecular motion of the peptide, and results in an increase in the FP values.

Reagents and Instruments

Enzyme: Human recombinant EE-tagged PDGFRβ, expressed in Sf9 cells (stock concentration 74.5 μM, from Protein Biochemistry, RDT); store at −80° C.

Substrate: Synthesized Fitc labeled peptide: FITC-ALTSN-QEYLDLSMPL; store at −20° C.

Positive Control Staurosporine (1 mM stock in DMSO, Calbiochem)

Robotic System Workstation: Tomtec Quadra

Reader: Acquest 384.1356 (Molecular Devices); FP reading method

Assay Plate: BD Falcon 30-μL 384 assay plate (Cat # 353972), and Costar 384 black plate (Cat # 3710)

Assay Procedures:
(1) Prepare Assay Buffer-MOPS Buffer: 20 mM MOPS (Teknova) pH 7.1, 5 mM sodium acetate, 6.25 mM $MgCl_2$, 0.5 mM EDTA, 1 mM DTT, 0.04 mM $NaVO_4$, 0.02% BSA.
(2) Prepare Substrate Mix containing peptide (1 μM) and ATP (48.6 μM) in assay buffer. Add 8 μL of Substrate Mix in BD Falcon assay plates.
(3) Prepare PDGFRβ (0.2 μM) in assay buffer.
(4) Dilute compounds and positive control in DMSO (40 fold, 4-pt in series). Add 18 μL/well of assay buffer into 384 polypropylene compound plates containing 2 μL of compound solution in each well, mix and transfer 4 μl/well of diluted solution into the BD Falcon assay plates containing 8 μL of Substrate Mix (step 2) in each well. Then add 4 μl/well of PDGFRβ solution (step 3) in all wells except blank wells. Add 4 μl/well of assay buffer into blank wells.
(5) Incubate at room temperature for 60 minutes.
(6) Prepare 1:400 IMAP bead mix following the instruction given in the IMAP Bead Binding System Kit (Molecular Devices), and add 30 μl/well of IMAP bead mix in Costar 384 black plates.
(7) Transfer 2 μl/well of reaction solution (step 4-5) into Costar 384 black plates containing 30 μl/well of bead mix (step 6).
(8) Incubate at RT for 2 hours.
(9) Read FP values at 485 nm and 530 nm on Acquest.
Kinase Enzyme Inhibition Assay ($IC_{50}$)

| Example | PDGFRβ $IC_{50}$ (μM) |
|---|---|
| 7 | 0.99 |
| 8 | 0.34 |
| 13 | 0.44 |
| 16 | 0.113 |
| 31 | <20 |

What is claimed:
1. A compound of the formula

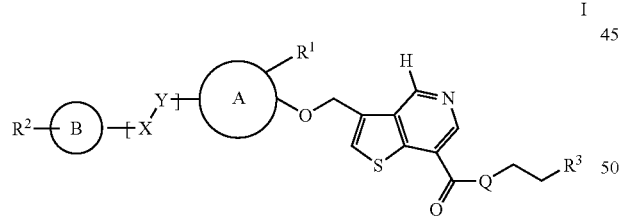

I wherein
$R^1$ is selected from the group consisting of hydrogen, lower alkyl, lower alkoxy, cyano, $NR^4R^5$, trifluoromethyl and $NO_2$;
$R^2$ is selected from the group consisting of hydrogen, lower alkyl, lower alkoxy, cyano, halogen, methyl sulfonyl, sulfonamide, trifluoromethyl, sulfonyl urea, amide, ester, carbamoyl, carbamate, $NR^4R^5$ and urea;
$R^3$ is selected from the group consisting of hydrogen, lower alkyl, hydroxyl, lower alkoxy and $NR^4R^5$;
$R^4$ and $R^5$ are selected from hydrogen, lower alkyl or lower alkyl substituted by hydroxyl or lower alkoxy;
Q is O or NH;
Ring A is aryl, Linker X—Y is selected from —NHCO— or —CONH—, or X—Y can be a simple bond;
Ring B is selected from group consisting of

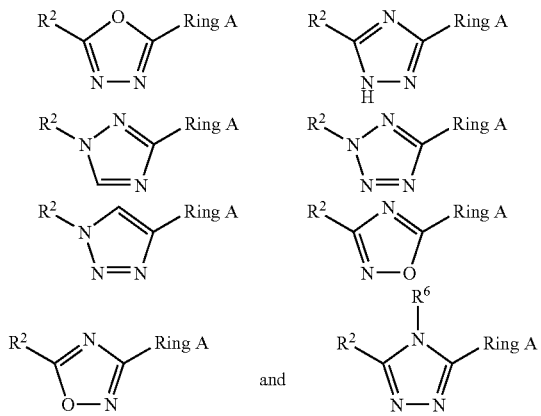

and wherein $R^6$ is lower alkyl substituted by hydroxy
or a pharmaceutically acceptable salts thereof.

2. The compound of claim 1 wherein Ring A is phenyl.

3. The compound of claim 1 wherein Ring A is 2,5-di-substituted phenyl.

4. The compound of claim 1 wherein $R^1$ is —$CH_3$.

5. The compound of claim 4 wherein $R^2$ is selected from the group consisting of —Cl, —F, —$CF_3$, —$CONH_2$, lower alkoxy, $NR^4R^5$, and lower alkyl.

6. The compound of claim 1 wherein X—Y is a simple bond.

7. The compound of claim 1 selected from the group consisting of
3-[3-(4-Chloro-benzoylamino)-phenoxymethyl]-thieno[3,2-c]Pyridine-7-carboxylic acid ethyl ester,
3-[3-(4-Chloro-benzoylamino)-phenoxymethyl]-thieno[3,2-c]pyridine-7-carboxylic acid (2-hydroxy-ethyl)-amide,
3-(3-Benzoylamino-phenoxymethyl)-thieno[3,2-c]pyridine-7-carboxylic acid ethyl ester,
3-(3-Benzoylamino-phenoxymethyl)-thieno[3,2-c]pyridine-7-carboxylic acid (2-hydroxy-ethyl)-amide,
3-[3-(4-Fluoro-benzoylamino)-phenoxymethyl]-thieno[3,2-c]pyridine-7-carboxylic acid ethyl ester,
3-[3-(4-Fluoro-benzoylamino)-phenoxymethyl]-thieno[3,2-c]pyridine-7-carboxylic acid (2-hydroxy-ethyl)-amide,
3-{3-[4-(2-Hydroxy-ethylamino)-benzoylamino]-phenoxymethyl}-thieno[3,2-c]pyridine-7-carboxylic acid (2-hydroxy-ethyl)-amide,
3-[3-(3-Chloro-benzoylamino)-phenoxymethyl]-thieno[3,2-c]pyridine-7-carboxylic acid ethyl ester,
3-[3-(2-Chloro-benzoylamino)-phenoxymethyl]-thieno[3,2-c]pyridine-7-carboxylic acid ethyl ester and
3-[3-(2-Fluoro-benzoylamino)-phenoxymethyl]-thieno[3,2-c]pyridine-7-carboxylic acid ethyl ester.

8. The compound of claim 1 selected from the group consisting of
3-[3-(3-Methoxy-benzoylamino)-phenoxymethyl]-thieno[3,2-c]pyridine-7-carboxylic acid ethyl ester,
3-[3-(2-Methoxy-benzoylamino)-phenoxymethyl]-thieno[3,2-c]pyridine-7-carboxylic acid ethyl ester,
3-[3-(4-Methoxy-benzoylamino)-phenoxymethyl]-thieno[3,2-c]pyridine-7-carboxylic acid ethyl ester, 3-[3-(3-Chloro-benzoylamino)-phenoxymethyl]-thieno[3,2-c]pyridine-7-carboxylic acid (2-hydroxy-ethyl)-amide,
3-[3-(2-Chloro-benzoylamino)-phenoxymethyl]-thieno[3,2-c]pyridine-7-carboxylic acid (2-hydroxy-ethyl)-amide,
3-[3-(2-Fluoro-benzoylamino)-phenoxymethyl]-thieno[3,2-c]pyridine-7-carboxylic acid (2-hydroxy-ethyl)-amide,
3-[3-(3-Methoxy-benzoylamino)-phenoxymethyl]-thieno[3,2-c]pyridine-7-carboxylic acid (2-hydroxy-ethyl)-amide,
3-[3-(4-Methoxy-benzoylamino)-phenoxymethyl]-thieno[3,2-c]pyridine-7-carboxylic acid (2-hydroxy-ethyl)-amide,
3-[3-(2-Hydroxy-benzoylamino)-phenoxymethyl]-thieno[3,2-c]pyridine-7-carboxylic acid (2-hydroxy-ethyl)-amide and
3-[5-(3-Chloro-benzoylamino)-2-methyl-phenoxymethyl]-thieno[3,2-c]pyridine-7-carboxylic acid ethyl ester.

9. The compound of claim 1 selected from the group consisting of
3-[5-(3-Chloro-benzoylamino)-2-methyl-phenoxymethyl]-thieno[3,2-c]pyridine-7-carboxylic acid (2-hydroxy-ethyl)-amide,
3-[5-(3-Chloro-benzoylamino)-2-methyl-phenoxymethyl]-thieno[3,2-c]pyridine-7-carboxylic acid (2-hydroxy-ethyl)-amide, toluene-4-sulfonic acid salt,
3-[5-(3-Fluoro-benzoylamino)-2-methyl-phenoxymethyl]-thieno[3,2-c]pyridine-7-carboxylic acid ethyl ester,
3-[5-(4-Fluoro-benzoylamino)-2-methyl-phenoxymethyl]-thieno[3,2-c]pyridine-7-carboxylic acid ethyl ester,
3-[5-(3-Methoxy-benzoylamino)-2-methyl-phenoxymethyl]-thieno[3,2-c]pyridine-7-carboxylic acid ethyl ester,
3-[5-(4-Fluoro-benzoylamino)-2-methyl-phenoxymethyl]-thieno[3,2-c]pyridine-7-carboxylic acid (2-hydroxy-ethyl)-amide,
3-[5-(3-Methoxy-benzoylamino)-2-methyl-phenoxymethyl]-thieno[3,2-c]pyridine-7-carboxylic acid (2-hydroxy-ethyl)-amide,
4-Chloro-3-[2-methyl-5-(5-methyl-[1,3,4]oxadiazol-2-yl)-phenoxymethyl]-thieno[3,2-c]pyridine-7-carboxylic acid ethyl ester,
3-[2-Methyl-5-(5-methyl-[1,3,4]oxadiazol-2-yl)-phenoxymethyl]-thieno[3,2-c]pyridine-7-carboxylic acid ethyl ester and
3-{5-[4-(2-Hydroxy-ethyl)-5-methyl-4H-[1,2,4]triazol-3-yl]-2-methyl-phenoxymethyl}-thieno[3,2-c]pyridine-7-carboxylic acid (2-hydroxy-ethyl)-amide.

10. A pharmaceutical composition comprising a compound of the formula wherein
$R^1$ is selected from the group consisting of hydrogen, lower alkyl, lower alkoxy, cyano, $NR^4R^5$, trifluoromethyl and $NO_2$;
$R^2$ is selected from the group consisting of hydrogen, lower alkyl, lower alkoxy, cyano, halogen, methyl sulfonyl, sulfonamide, trifluoromethyl, sulfonyl urea, amide, ester, carbamoyl, carbamate, $NR^4R^5$ and urea;
$R^3$ is selected from the group consisting of hydrogen, lower alkyl, hydroxyl, lower alkoxy and $NR^4R^5$;
$R^4$ and $R^5$ are selected from hydrogen, lower alkyl or lower alkyl substituted by hydroxyl or lower alkoxy;
Q is O or NH;
Ring A is aryl;
Linker X—Y is —NHCO— or —CONH—, X—Y can be a simple bond;
Ring B is selected from group consisting of wherein $R^6$ is lower alkyl substituted by hydroxyl or a pharmaceutically acceptable salts thereof together with a pharmaceutically acceptable excipient.

* * * * *